United States Patent
Tanaka et al.

[11] Patent Number: 6,048,464
[45] Date of Patent: Apr. 11, 2000

[54] FILTER MEDIUM FOR LEUKOCYTE REMOVAL, METHOD OF MAKING, AND METHOD OF USING THEREOF

[75] Inventors: Jun Tanaka; Tatsuya Fukuda, both of Oita; Kumi Yoshida, Saiki, all of Japan

[73] Assignee: Asahi Medical Co., Ltd., Tokyo, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/894,320
[22] PCT Filed: Dec. 26, 1996
[86] PCT No.: PCT/JP96/03814
§ 371 Date: Aug. 14, 1997
§ 102(e) Date: Aug. 14, 1997
[87] PCT Pub. No.: WO97/23266
PCT Pub. Date: Jul. 3, 1997

[30] Foreign Application Priority Data
Dec. 26, 1995 [JP] Japan .................................. 7-350718

[51] Int. Cl.[7] .......................... B01D 37/00; B01D 29/00; B01D 39/00
[52] U.S. Cl. .......................... 210/767; 210/488; 210/490; 210/491; 210/503; 210/504; 210/505; 210/506; 210/507; 210/508; 264/172.11; 264/172.17; 264/DIG. 48; 435/2; 435/170; 435/823
[58] Field of Search .................................. 210/767, 435, 210/446, 488, 489, 490, 491, 503, 504, 505, 506, 507, 508, 645; 264/172.11, 172.17, DIG. 48; 435/2, 101, 170, 823; 428/293.4, 295.1, 296.4, 297.4, 297.7, 300.1, 300.7

[56] References Cited

U.S. PATENT DOCUMENTS

| | | | |
|---|---|---|---|
| 3,593,854 | 7/1971 | Swank | 210/446 |
| 4,701,267 | 10/1987 | Watanabe et al. | 210/505 |
| 4,936,998 | 6/1990 | Nishimura et al. | 210/508 |
| 5,290,449 | 3/1994 | Heagle et al. | 210/508 |
| 5,298,165 | 3/1994 | Oka et al. | 210/505 |
| 5,407,581 | 4/1995 | Onodera et al. | 210/508 |
| 5,456,835 | 10/1995 | Castino et al. | 210/645 |
| 5,478,470 | 12/1995 | Fukuda et al. | 210/508 |
| 5,591,337 | 1/1997 | Lynn et al. | 210/496 |
| 5,639,376 | 6/1997 | Lee et al. | 210/645 |
| 5,665,233 | 9/1997 | Fukuda et al. | 210/506 |
| 5,681,469 | 10/1997 | Barboza et al. | 210/508 |
| 5,817,237 | 10/1998 | Lee et al. | 210/645 |

FOREIGN PATENT DOCUMENTS

| | | |
|---|---|---|
| 0 155003 A2 | 9/1985 | European Pat. Off. . |
| 0 612550 A1 | 8/1994 | European Pat. Off. . |
| A56-53616 | 5/1981 | Japan . |
| A2-46857 | 2/1990 | Japan . |
| A5-15584 | 1/1993 | Japan . |
| 5-229063 | 9/1993 | Japan . |
| A6-24995 | 2/1994 | Japan . |
| A6-63131 | 3/1994 | Japan . |
| A7-31677 | 2/1995 | Japan . |
| 93 01880 | 2/1993 | WIPO . |

*Primary Examiner*—John Kim
*Attorney, Agent, or Firm*—Birch, Stewart, Kolasch & Birch, LLP

[57] ABSTRACT

A leukocyte-removing filter material is described, which includes a porous element having fine pores of an average pore diameter of not less than 1.0 μm but less than 100 μm and a fiber structure composed of a plurality of fibers having an average fiber diameter of not less than 0.01 μm but less than 1.0 μm kept on the porous element. The porosity of the filter material is not less than 50% but less than 95%, and the proportion of the fiber structure to the filter material is not less than 0.01% by weight but less than 30% by weight. The ratio between the average pore diameter of the porous element and the average fiber diameter of the fiber structure is not less than 2 but less than 2,000 and the above fiber structure forms a reticulate structure. A process for producing the leukocyte-removing fiber material and an apparatus for removing leukocyte using the above fiber material are also described.

53 Claims, 2 Drawing Sheets

FILTER MEDIUM FOR LEUKOCYTE REMOVAL, METHOD OF MAKING, AND METHOD OF USING THEREOF

TECHNICAL FIELD

This invention relates to a leukocyte-removing filter material for removing leukocyte from a leukocyte-containing solution, a process for producing the same, a leukocyte-removing apparatus using the same and a process for removing leukocyte.

BACKGROUND ART

In the field of a blood transfusion, in addition to the so-called whole blood transfusion that a whole blood preparation prepared by adding an anticoagulant to blood gathered from donors is transfused, a so-called blood component transfusion has heretofore been generally carried out by which the blood component which the recipient requires separated from the whole blood preparation is transfused into the recipient. The blood component transfusion includes erythrocyte transfusion, platelet transfusion, plasma transfusion and the like depending upon the kind of blood component required by a recipient, and the blood component preparations used in these transfusions include erythrocyte preparation, platelet preparation, plasma preparation and the like. Recently, a so-called leukocyte-removed blood transfusion has been spread by which a blood preparation is transfused after the leukocyte mixed in the blood component preparation has been removed. This is because it has been clarified that relatively light side effects such as headache, nausea, chill, non-hemolytic febrile transfusion reaction and the like which accompany the blood transfusion; grave side effects such as alloantigen sensitization, virus infection, post-transfusion GVHD and the like which seriously affect the recipient are caused mainly by the leukocyte mixed in a blood preparation used in the blood transfusion.

In order to prevent the relatively light side effects including headache, nausea, chill, fever and the like, it is said that the removal of the leukocyte in a blood preparation until the proportion of the residual leukocyte becomes $10^{-1}$ to $10^{-2}$ or less is sufficient. Also, in order to prevent the alloantigen sensitization and virus infection which are grave side effects, it is said that the removal of the leukocyte until the proportion of the residual leukocyte becomes $10^{-4}$ to $10^{-6}$ or less is sufficient.

The method of removing leukocyte from a blood preparation is roughly classified into two methods, one of which is a centrifuging method by which leukocyte is separated and removed by utilizing the specific gravity difference of blood components by using a centrifugal separator and a filtering method by which leukocyte is removed using a filter material consisting of a porous element such as a fibrous material, a porous material having interconnected cells or the like. The filtering method has such advantages as excellent leukocyte-removing performance, simple operation, low cost, etc., so that the filtering method has been spread. Moreover, as the filtering method, a method which comprises removing leukocyte by sticking or adsorbing using a nonwoven fabric as a filter material is now the most spreading because this method is particularly excellent in leukocyte-removing performance.

The mechanism of removing leukocyte by a filter apparatus using the above-mentioned fibrous material or porous material is mainly attributed to the fact that the leukocyte which has contacted with the surfaces of the filter material sticks to or adheres to the surfaces of the filter material. For example, EP-A-0155003 discloses a technique by which a nonwoven fabric is used as the filter material. Furthermore, WO93/01880 discloses a leukocyte-removing filter material produced by dispersing in a dispersion medium a mass of a great number of small fiber pieces having a fiber diameter of not more than 0.01 μm and a length of about 1 to 50 μm, together with spinable and weavable short fibers having a fineness of about 0.05 to 0.75 d and an average length of 3 to 15 mm, and removing the dispersion medium from the resulting dispersion.

The existing leukocyte-removing filter has such a leukocyte-removing performance as to decrease the number of the residual leukocytes to not more than $1\times10^5$. Under such circumstances, two demands for the leukocyte-removing filter have been brought up in the market.

The first demand is to enhance the recovery of the useful component and improve the handling by rendering the operation of recovering the useful component remaining in the filter and the circuit unnecessary by the presence of a physiological saline solution and air. In particular, blood which is the starting material for the blood preparation is in many cases a precious one supplied by well-intentioned blood donation, and the blood which has remained in the filter and has become impossible to recover is scrapped as it is, together with the filter and goes to waste. Therefore, it is very significant to increase the recovery of the useful component as compared with the existing leukocyte-removing filter. However, in the case of the leukocyte-removing filter using the conventional technique, it is difficult to very greatly increase the recovery of the useful component.

The second demand is to achieve a higher leukocyte-removing rate than the existing leukocyte-removing filter and completely prevent a grave side effect from being caused by the leukocyte transfused into a patient. However, with the leukocyte-removing filter using the conventional technique, it is difficult to achieve so high a leukocyte-removing rate that such a side effect can be completely prevented.

DISCLOSURE OF INVENTION

The first object of this invention is to provide a leukocyte-removing filter material which is much higher in leukocyte-removing performance per unit volume than the conventional filter material and in which the flow of a leukocyte-containing solution is good. This filter material is a leukocyte-removing filter material which comprises a porous element having fine pores of an average pore diameter of not less than 1.0 μm but less than 100 μm and a fiber structure composed of a plurality of fibers having an average fiber diameter of not less than 0.01 μm but less than 1.0 μm kept on the above porous element and in which the porosity of the above filter material is not less than 50% but less than 95%; the proportion of the above fiber structure to the said filter material (the word "proportion" is called "keeping proportion" hereinafter) is not less than 0.01% by weight but less than 30% by weight; the ratio between the average pore diameter of the pores of the above porous element (referred to in some cases hereinafter as the average pore diameter of the porous element) and the average fiber diameter of the fibers constructing the above fiber structure (referred to in some cases hereinafter as the average fiber diameter of the fiber structure) is not less than 2 but less than 2,000; and the above fiber structure forms a reticulate structure. The present inventors have found that when such a leukocyte-removing filter material is used, the above-mentioned first object can be achieved.

The second object of this invention is to provide a process for producing the leukocyte-removing filter material of this invention. This process is a process for producing a filter material in which fibers having an average fiber diameter of not less than 0.01 μm but less than 1.0 μm obtained by cleaving cleavable fibers are dispersed in a solvent and deposited and kept on a porous element having fine pores of an average pore diameter of not less than 1.0 μm but less than 100 μm (referred to in some cases hereinafter as the porous element having an average pore diameter of not less than 1.0 μm but less than 100 μm); a process for producing a filter material comprising allowing a microorganism having an ability to produce cellulose fiber and a porous element having an average pore diameter of not less than 1.0 μm but less than 100 μm to coexist in a liquid culture medium and culturing the microorganism; or the like. The present inventors have found that according to such a process, the leukocyte-removing filter material of this invention can be produced very effectively.

The third object of this invention is to provide a filter apparatus for removing leukocyte which can remove leukocyte from a leukocyte-containing solution such as a whole blood preparation, an erythrocyte preparation, a platelet preparation or the like while inhibiting the loss of the useful blood component very low, and achieve a high leukocyte-removing rate; and a process for removing leukocyte. The present inventors have found that when a leukocyte-containing solution is filtered by means of the filter apparatus for removing leukocyte in which a leukocyte-removing filter material is appropriately arranged which consists of a porous element having an average pore diameter of not less than 1.0 μm but less than 100 μm and a fiber structure composed of a plurality of fibers having an average fiber diameter of not less than 0.01 μm but less than 1.0 μm kept on the above porous element (said fiber structure is referred to hereinafter as the fiber structure having an average fiber diameter of not less than 0.01 μm but less than 1.0 μm) and in which the porosity of the filter material is not less than 50% but less than 95%; the keeping proportion of the above fiber structure to the above filter material is not less than 0.01% by weight but less than 30% by weight; the ratio between the average pore diameter of the above porous element and the average fiber diameter of the above fiber structure is not less than 2 but less than 2,000; and the above fiber structure forms a reticulate structure, the loss of the useful blood component can be lowered and a high leukocyte-removing rate can be achieved.

The present inventors have made extensive research in order to achieve the above objects, and have consequently completed this invention relating to a leukocyte-removing filter material which consists of a porous element having an average pore diameter of not less than 1.0 μm but less than 100 μm and a fiber structure of an average fiber diameter of 0.01 μm but less than 1.0 μm kept on the above porous element and in which the porosity of the above filter material is not less than 50% but less than 95%; the keeping proportion of the above fiber structure to the above filter material is not less than 0.01% by weight but less than 30% by weight; the ratio between the average pore diameter of the above porous element and the average fiber diameter of the above fiber structure is not less than 2 but less than 2,000; and the above fiber structure forms a reticulate structure.

BEST MODE FOR CARRYING OUT THE INVENTION

The average fiber diameter referred to in this invention is a value obtained by taking a scanning electron micrograph of fibers constructing the fiber structure, measuring diameters of at least 100 fibers selected at random and calculating the number average value of them. The measurement of the average fiber diameter may be carried out before keeping the fibers on the porous element which is a base material or after keeping the fibers on the porous element which is a base material. In particular, when the porous element is composed of a congregation of fibers, it is preferable to measure the average fiber diameter before keeping the fibers on the porous element because the measurement can be more exactly carried out.

Fibers having an average fiber diameter of less than 0.01 μm have a low fiber strength, and when a leukocyte-containing solution is treated, the fibers tend to be cut by collision of leukocyte, other blood cell components or the like, so that the above fibers are not suitable for the purpose of this invention. Moreover, fibers having an average fiber diameter of not less than 1.0 μm make the porosity of the filter material smaller, whereby the flow of a leukocyte-containing solution becomes bad, so that the above fibers are not suitable for the purpose of this invention. In order to contact lymphocyte and the like, which have a relatively small diameter among the leukocytes and are low in tackiness, with the filter material at many points with a good efficiency and capture them, the average fiber diameter of the fibers is preferably not less than 0.01 μm but less than 0.8 μm.

Figure 1:
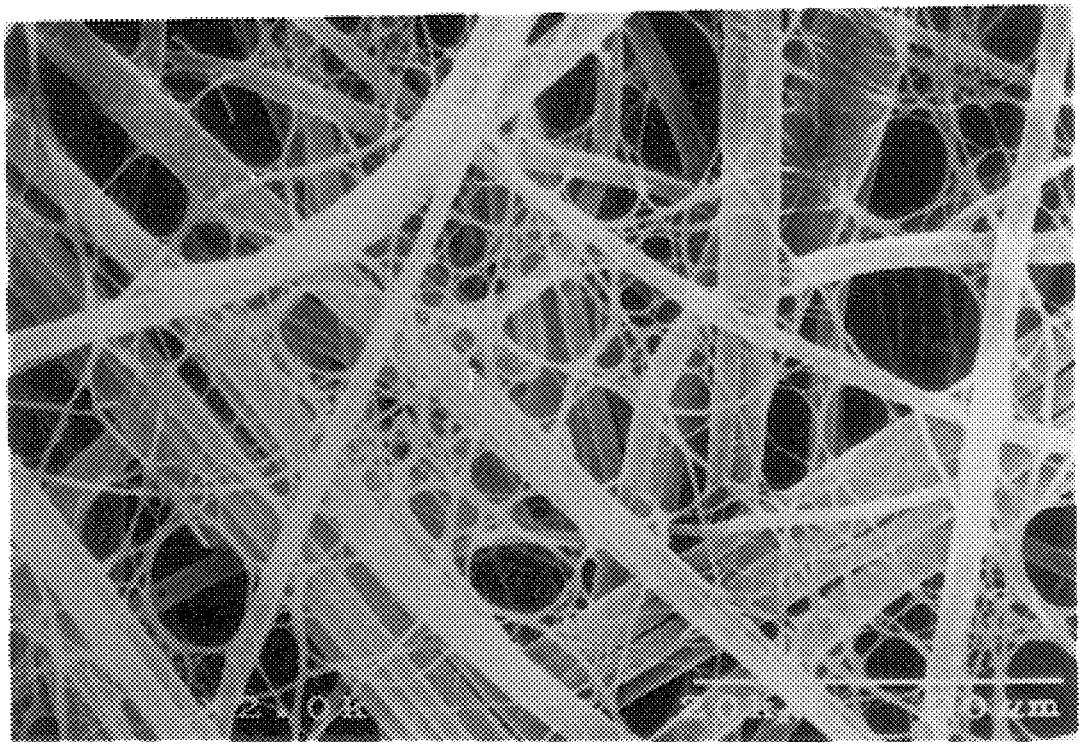
FIG. 1 is an electron micrograph of a filter material having a curved reticulate structure.
Figure 2:
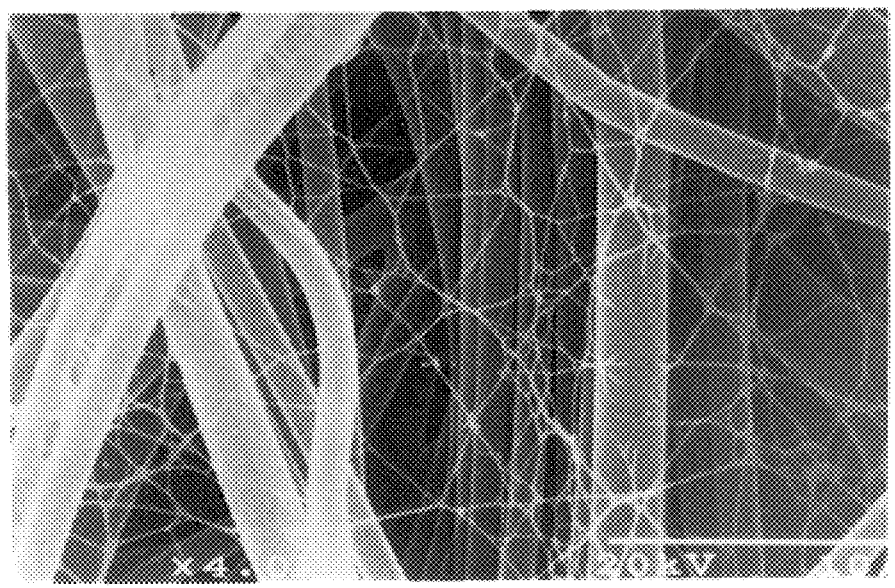
FIG. 2 is an electron micrograph of a filter material having a polygonal reticulate structure.

In addition, in the fiber structure in this invention, fibers having a very small average fiber diameter form a reticulate structure. Such a reticulate fiber structure is kept on the porous element. In this invention, that the fiber structure is kept on the porous element means the state that the above reticulate fiber structure is present so that the pore portions of the porous element which is a base material are covered therewith and is fixed on the base material as shown in FIG. 1 or FIG. 2. FIG. 1 and FIG. 2 are electron micrographs of the filter materials of this invention having typical reticulate structures. Based on FIG. 1 and FIG. 2, the characteristics in physical structure of the filter material of this invention are described below.

In the filter material of this invention, a plurality of fibers having an average fiber diameter of not less than 0.01 μm but less than 1.0 μm form a reticulate structure and constitute the fiber structure, and this fiber structure is kept on a porous element having fine pores having an average pore diameter of not less than 1.0 μm but less than 100 μm. However, the fibers constituting the fiber structure are not in the form a bundle but in the form of a so-called single fiber in which the fibers are in the split state, and a plurality of these single fibers are physically entangled to form a reticulate structure. The reticulate structure referred to in this invention includes such a structure that the formed meshes are curved because the fibers constituting the fiber structure have a curved structure as represented by FIG. 1, and such a structure that the meshes formed are polygonal because the fibers constituting the fiber structure have a linear structure as represented by FIG. 2.

When this reticulate fiber structure is uniformly kept on the porous element at the cross-section perpendicular to the flow of the leukocyte-containing solution, the leukocyte can be captured with a good efficiency, so that it is preferred. That the fiber structure is uniformly kept on the porous element at the cross-section perpendicular to the flow of the leukocyte-containing solution means that when portions of filter material in the cross-section perpendicular to the flow of the leukocyte-containing solution are sampled at random, the amount (density) of the fiber structure contained in each of those sampled portions of filter material is substantially equal, and this amount introduced can be actually determined by measuring the scattering of amount of the fiber structure present in a given amount of the filter material in each portion of the filter material sampled.

Furthermore, it is particularly preferable that in addition to the substantially equal amount of the fiber structure introduced in each portion of the filter material sampled at random in the cross-section perpendicular to the flow of the leukocyte-containing solution, the distribution of mesh sizes in each portion is substantially equal and a substantially same reticulate structure is formed. Incidentally, in the present specification, such a state is expressed "a uniform, reticulate structure is formed". More specifically explaining, that a uniform, reticulate structure is formed refers to such a state that the reticulate structure in each portion of the filter material sampled at random has, when observed through an electron microscope, a distribution of approximate mesh sizes and a similar mesh form and is deemed to be substantially the same. The state that no uniform reticulate structure is formed refers to such a state that when the reticulate structure in each portion of the filter material sampled at random is observed, it can be judged that the distribution of mesh sizes in each portion is greatly different and the form thereof is clearly different.

In the filter material of this invention, it is preferable that the fiber structure having an average fiber diameter of not less than 0.01 $\mu$m but less than 1.0 $\mu$m forms a reticulate structure and is kept on the porous element having an average pore diameter of not less than 1.0 $\mu$m but less than 100 $\mu$m; the porosity of the filter material is not less than 50% but less than 95%; and the ratio between the average pore diameter of the porous element and the average fiber diameter of the fiber structure is not less than 2 but less than 2,000.

Here, the average pore diameter is a value obtained by measurement according to a mercury pressurizing method. That is to say, when the amount of mercury pressurized at a mercury-pressurizing pressure of 1 psia is 0% and the amount of mercury pressurized at a mercury pressurizing pressure of 265 psia is 100%, a fine pore diameter corresponding to an amount of mercury pressurized of 50% is taken as the average pore diameter. When the average pore diameter is less than 1.0 $\mu$m, the leukocyte-containing solution does not flow and hence it is not suitable for the purpose of this invention. When the average pore diameter is not less than 100 $\mu$m, it often becomes difficult to maintain the fiber structure and hence it is not suitable for the purpose of this invention.

In order to keep the flow of the leukocyte-containing solution in a good state, the ratio between the average pore diameter of the porous element and the average fiber diameter of the fiber structure is preferably not less than 2 but less than 2,000. When the ratio between the average pore diameter of the porous element and the average fiber diameter of the fiber structure is less than 2, there is substantially no difference between the fine pore diameter of the porous element and the diameters of fibers constituting the fiber structure and the fine pores of the porous element are blocked with the fibers and consequently the flow of the leukocyte-containing solution becomes very bad. Therefore, it is not suitable for the purpose of this invention. When the ratio of the average pore diameter of the porous element and the average fiber diameter of the fiber structure is not less than 2,000, the diameters of fine pores of the porous element are large and it becomes difficult to keep the fiber structure so that the fine pores of the porous element are covered with the fiber structure and an extreme decrease of the leukocyte-removing performance is brought about. In addition thereto, the entanglement of the fiber structure with the porous element becomes insufficient and there is a fear that the fiber structure falls away, so that it is not suitable. It is more preferable that the ratio between the average pore diameter of the porous element and the average fiber diameter of the fiber structure is not less than 10 but less than 1,800.

The porous element referred to in this invention includes a fiber congregation, a porous film, a spongy, interconnected, porous material and the like which have an average pore diameter of not less than 1 $\mu$m but less than 100 $\mu$m. As the porous element, preferable is the above fiber congregation, particularly preferable is a fiber congregation consisting of long fibers. The form of the fiber congregation is preferably a nonwoven fabric, a woven fabric, a knitted fabric or the like; however, particularly preferable is a nonwoven fabric. When the porous element is a fiber congregation, it is particularly preferable that the ratio of the average fiber diameter of the fiber congregation to the average fiber diameter of the fiber structure is not less than 10 but less than 1,000 in order to keep the flow of the leukocyte-containing solution in a good state. As the material of the porous element, there can be used any material which can form a nonwoven fabric, a woven fabric, a knitted fabric, a porous film, a spongy, interconnected, porous material or the like, such as polyurethane, polyester, polyolefin, polyamide, polystyrene, polyacrylonitrile, cellulose, cellulose acetate or the like.

Moreover, in the leukocyte-removing filter material of this invention, it is preferable that the keeping proportion of the fiber structure to the filter material is not less than 0.01% by weight but less than 30% by weight. When the keeping proportion is less than 0.01% by weight, there is not obtained a sufficient amount of fibers for capturing the leukocyte in a leukocyte-containing solution, so that it is not suitable for the purpose of this invention. When the keeping proportion is not less than 30% by weight, the amount of fibers introduced into the porous element becomes too large, and the fine pore portions of the porous element are blocked, whereby the leukocyte-containing solution does not flow, so that it is not suitable for the purpose of this invention. The keeping proportion of the fiber structure to the filter material is more preferably not less than 0.03% by weight but less than 10% by weight.

The measurement of the keeping proportion can be determined from the weight change before and after keeping the fiber structure on the porous element. Also, when the keeping proportion of the fiber structure is as small as less than about 3% by weight per unit weight of the filter material, there can be used, for more precisely determining the keeping proportion of the fiber structure than the above weight measurement, a method by which only the fiber structure is dissolved and abstracted and the amount of the abstracted component is determined. Referring to the case where the fiber structure is composed of cellulose as an example, a method of determining the amount thereof is specifically explained below. The leukocyte-removing filter material of this invention is immersed and shaken in a solution of cellulase to decompose the cellulose of the fiber structure into glucose and the glucose is extracted. The extracted glucose is subjected to quantitative determination using a commercially available quantitative determination reagent, and from the amount of glucose obtained, the amount of fiber structure kept on the porous element is calculated.

In order to achieve a high leukocyte-removing performance, it is preferable that the fiber structure is kept over the whole of the porous element. However, when it is difficult that the fiber structure is kept in a deep interior of the porous element because of a limit resulting from production process, the fiber structure may be kept on the surface of one side of the porous element, and in such a case, as a means for simply enhancing the leukocyte-removing performance of the filter material by increasing the keeping proportion of the fiber structure, the fiber structure may be kept on the surfaces of both sides of the porous element. In either case, it is preferable to substantially uniformly keep the fiber structure on the porous element in order to achieve the high leukocyte-removing performance.

In the leukocyte-removing filter material of this invention, it is preferable that the porosity is not less than 50% but less than 95%. When the porosity of the filter material is less than 50%, the flow of the leukocyte-containing solution is bad and it is not suitable for the purpose of this invention. When the porosity is not less than 95%, the mechanical strength of the filter material is low and when the leukocyte-containing solution is treated, the filter material is broken and no more exerts its function as a filter material, so that it is not suitable for this invention.

The porosity is determined by measuring the dry weight ($W_1$) of the filter material cut to the given area; further measuring the thickness; calculating the volume (V), immersing this filter material in water, subjecting the same to deaeration; thereafter measuring the weight ($W_2$) of the water-containing filter material; and calculating the porosity from the following calculating equation in which $\rho$ is the density of pure water:

$$\text{Porosity }(\%) = (W_2 - W_1) \times \rho \times 100 / V.$$

The thickness of the leukocyte-removing filter material of this invention is preferably not less than 0.1 mm but less than 30 mm in the direction of the flow of the leukocyte-containing solution. When the thickness is less than 0.1 mm, the frequency of collision between the filter material and the leukocyte in the leukocyte-containing solution is reduced, and hence, a high leukocyte-removing performance is difficult to achieve, so that it is not desirable. When the thickness is not less than 30 mm, the resistance of the filter material to the passing of the leukocyte-containing solution therethrough becomes high, and hence, the treatment time is elongated and the erythrocyte membrane is broken to cause hemolysis, and for these reasons and the like, it is not desirable. It is more preferable that the thickness of the filter material in the flow direction is not less than 0.1 mm but less than 15 mm.

When as a method of obtaining the filter material of this invention, there is adopted a production process characterized by dispersing the fibers having an average fiber diameter of not less than 0.01 $\mu$m but less than 1.0 $\mu$m in a solvent and keeping the same, by paper-making, on a porous element having an average pore diameter of not less than 1.0 $\mu$m but less than 100 $\mu$m, it is more preferable that in the leukocyte-removing filter material obtained, the ratio of the average pore diameter of the porous element to the average fiber diameter of the fiber structure is not less than 16 but less than 300. Moreover, the keeping proportion of the fiber structure to the filter material is preferably not less than 0.3% by weight but less than 5.0% by weight. In addition, it is more preferable that the average fiber diameter of the fiber structure is not less than 0.05 $\mu$m but less than 0.5 $\mu$m.

Furthermore, when as a method of obtaining the filter material of this invention, there is adopted a production process characterized by allowing a microorganism having an ability to produce cellulose fiber and a porous element having an average pore diameter of not less than 1.0 $\mu$m to less than 100 $\mu$m to coexist in a liquid culture medium, culturing the microorganism in the liquid culture medium and recovering the porous element, it is preferable that in the leukocyte-removing filter material obtained, the ratio of the average pore diameter of the porous element to the average fiber diameter of the fiber structure is not less than 160 but less than 1,500. In addition, it is more preferable that the keeping proportion of the fiber structure to the filter material is not less than 0.03% by weight but less than 1.0% by weight, and it is more preferable that the average fiber diameter of the fiber structure is not less than 0.01 $\mu$m but less than 0.05 $\mu$m.

Since when the leukocyte-removing filter material of this invention is treated, as a post-processing, with a binding agent such as a water-insoluble high polymer solution or the like, there is generally a possibility that the reticulate structure is broken, including the case where the fibers constructing the fiber structure are bundled with one another in the form of a bundle, the case where a film-like material is formed between plural fibers, and the like, so that it is preferable that the filter material is not treated with such a binding agent. On the other hand, when the fibers are relatively thick and short and the physical entanglement thereof with the porous element is insufficient, it is possible to effectively fix the fibers on the porous element by a treatment with a binding agent such as a relatively dilute, water-insoluble high polymer solution or the like as a post-processing of the leukocyte-removing filter material of this invention, whereby the fibers can be prevented from falling off.

It is also possible to modify the surface of the leukocyte-removing filter material to a surface to which platelet or erythrocyte is difficult to stick, thereby increasing the recovery of the platelet or erythrocyte and removing only the leukocyte. As a method of modifying the surface of the filter material, there are mentioned a surface graft-polymerization, a coating with a high polymer material, an electrical discharge treatment and the like.

As the high polymer material used when the surface of the filter material is modified by a surface graft-polymerization or a coating with a high polymer material, preferred is a high polymer material having a nonionic hydrophilic group. As the nonionic hydrophilic group, there are mentioned hydroxyl group, amido group, polyethylene oxide chain and the like. The monomers which can be used in the synthesis of the high polymer material having a nonionic hydrophilic group include, for example, 2-hydroxyethyl methacrylate, 2-hydroxyethyl acrylate, vinyl alcohol (prepared by hydrolyzing a polymer obtained by polymerization of vinyl acetate), methacrylamide, N-vinylpyrrolidone and the like. Among the above monomers, 2-hydroxyethyl methacrylate and 2-hydroxyethyl acrylate are preferred in view of easy availability, easy handling in the polymerization, leukocyte-containing solution-treating performance, and the like.

The high polymer material used in the above surface graft-polymerization or in the coating with a high polymer material is preferably a copolymer containing, as a monomeric unit, a polymerizable monomer having a nonionic hydrophilic group and/or a basic nitrogen-containing functional group in an amount of 0.1 to 20 mole %. As the basic nitrogen-containing functional group, there are mentioned primary amino group, secondary amino group, tertiary amino group, quaternary ammonium group and the like; and also nitrogen-containing aromatic ring group such as pyridyl group, imidazole group and the like; etc. As the polymerizable monomer having a basic nitrogen-containing functional group, there can be mentioned derivatives of methacrylic acid such as dimethylaminoethyl methacrylate, diethylaminoethyl methacrylate, dimethylaminopropyl methacrylate, 3-dimethylamino-2-hydroxypropyl methacrylate and the like; vinyl derivatives of nitrogen-containing aromatic compounds such as allylamine, p-vinylpyridine, 4-vinylimidazole and the like; and quaternary ammonium salts obtained by reacting the above vinyl compound with an alkyl halide or the like. Among the above polymerizable monomers, dimethylaminoethyl methacrylate and diethylaminoethyl methacrylate are preferred from the viewpoints of easy availability, easy handling in polymerization, leukocyte-containing solution-treating performance and the like.

When the monomer unit content of the polymerizable monomer having a basic nitrogen-containing functional group in the copolymer obtained is less than 0.1%, the effect of inhibiting platelet from sticking to the surface of the filter material is not so much found, and hence, it is not desirable. Moreover, when the monomer unit content of the polymerizable monomer having a basic nitrogen-containing functional group in the copolymer is not less than 20%, not only leukocyte but also useful components such as platelet and erythrocyte become liable to stick to the surface of the filter material, and hence, it is not desirable. It is more preferable that the content of the polymerizable monomer having a basic nitrogen-containing functional group in the copolymer is 0.2 to 5% as the monomer unit.

The present inventors have made extensive research on providing a process for producing a leukocyte-removing filter material which is the second object of this invention and have consequently found that when fibers having an average fiber diameter of not less than 0.01 $\mu$m but less than 1.0 $\mu$m are dispersed in a dispersion medium and kept, by paper-making, on a porous element having an average pore diameter of not less than 1.0 $\mu$m but less than 100 $\mu$m, there can be produced a leukocyte-removing filter material which consists of the above porous element and a fiber structure composed of a plurality of the fibers and in which the porosity of the above filter material is not less than 50% but less than 95%, the keeping proportion of the above fiber structure to the above filter material is not less than 0.01% by weight but less than 30% by weight, the ratio between the average pore diameter of the above porous element and the average fiber diameter of the above fiber structure is not less than 2 but less than 2,000 and the above fiber structure forms a reticulate structure, and have completed the production process of this invention.

In order for the fiber structure to form a reticulate structure in the filter material of this invention, it is necessary that the fibers having an average fiber diameter of not less than 0.01 $\mu$m but less than 1.0 $\mu$m have a curved shape and have such properties that the fibers per se are soft, easy to curve, relatively short and the like. In addition, even if fibers originally do not have a curved shape, they are applicable to this invention as far as they have been given a curved shape by a heat treatment, a mechanical treatment or a treatment with various chemicals.

The above fibers having an average fiber diameter of not less than 0.1 $\mu$m but less than 1.0 $\mu$m can be produced by subjecting dividable fibers, representatives of which are regenerated cellulose fiber, finely porous cleavable acrylic fiber and the like, as well as the cleavable composite fibers obtained by the known methods stated in JP-B-47-37648, JP-A-50-5650, JPA-53-38709 and the like, to physical stir using a mixer or the like, ejection of a high pressure liquid stream, treatment in a high pressure homogenizer, or the like.

As the material of fiber which can be easily curved, suitable are cellulose, polyacrylonitrile, polyester, polyolefin, polyamide and the like; however, there can be used any material which can be formed into fibers which have an average fiber diameter of not less than 0.01 $\mu$m but less than 1.0 $\mu$m and can be curved by a heat treatment or a mechanical treatment.

A method for obtaining fibers having the above specified average fiber diameter by subjecting, among the above-mentioned dividable fibers, regenerated cellulose fibers, if necessary, to acid treatment or alkali treatment and thereafter to physical stir in a liquid using a mixer or the like to fibrillate the fibers is particularly preferable, because the fiber diameters of the resulting fibers become very small, and fibers having a curved form can be easily obtained, as a result of which it becomes easy for the fibers to form a reticulate structure. This process for obtaining fibers having an average fiber diameter of not less than 0.01 $\mu$m but less than 1.0 $\mu$m by fibrillating regenerated cellulose fibers is explained below specifically and in more detail. First of all, commercially available regenerated cellulose fibers having fiber diameters of about 10 $\mu$m are cut to a given length, and thereafter immersed in about 3% by weight aqueous sulfuric acid solution and subjected to acid treatment at 70° C. for 30 minutes with slowly stirring. The thus acid-treated regenerated cellulose fibers are washed with water and thereafter vigorously stirred in water using a mixer at 10,000 rpm for a period of from 30 minutes to 90 minutes, upon which the regenerated cellulose fibers are fibrillated and made finer, whereby the objective fibers can be finally obtained.

Also, fibers having an average fiber diameter of not less than 0.01 $\mu$m but less than 1.0 $\mu$m obtained by using a known sea-island type fibers as the starting material, subjecting them, if necessary, to previous heat treatment or mechanical treatment to process the starting fibers into a curved shape and dissolving the sea component using various solvents to remove the same, have also a curved shape and are suitable for the production of the above-mentioned leukocyte-removing filter material of this invention.

Other processes for obtaining fibers suitable for the production of the leukocyte-removing filter material of this invention are described below.

Microorganisms having an ability to produce cellulose are cultured by intermittently or continuously giving them a vibration in a liquid culture medium. When a vibration is given, the microorganisms having an ability to produce cellulose can cut and separate the cellulose fibers produced from the bacterial cells. In general, with acetic acid bacterium which is a kind of microorganism having an ability to produce cellulose, it is said that the fiber diameters of the cellulose fibers produced are about 0.01 $\mu$m to about 0.1 $\mu$m and the cellulose fiber-production rate is about 2 $\mu$m/min. Accordingly, by suitably setting the time for which a vibration is given to the liquid culture medium and the interval thereof, fibers having the desired length can be obtained. By recovering these fibers from the culture medium, there can be also obtained fibers suitable for the production of the leukocyte-removing filter material of this invention. Furthermore, in order to enhance the dispersibility of the fibers obtained by intermittently or continuously giving a vibration to microorganisms having an ability to produce cellulose while culturing the microorganisms in a liquid culture medium, it is preferable to split the fibers by such a means as violently stirring of the liquid culture medium or the like. Also, when the microorganisms having an ability to produce cellulose are continued to be cultured in a liquid culture medium for a long period of time, a gel-like fiber mass in which a number of cellulose fibers congregate is obtained. By finely grinding and splitting this gel-like fiber mass in a homogenizer or the like, fibers suitable for the production of the leukocyte-removing filter material of this invention can also be obtained.

The thus obtained fibers having an average fiber diameter of not less than 0.01 $\mu$m but less than 1.0 $\mu$m are dispersed in a dispersion medium so that the concentration becomes about 0.01 g/L to about 1 g/L to obtain a fiber dispersion. As the dispersion medium, there can be used not only pure water but also an aqueous solution containing about 0.1% to 5% of a surfactant; an aqueous solution whose viscosity has been increased by adding thereto about 0.1% to 5% of a polyacrylamide for more improving the dispersibility of the fibers; and the like.

Subsequently, a porous element having an average pore diameter of not less than 1.0 $\mu$m but less than 100 $\mu$m is arranged on the base of a funnel-like vessel and the above fiber dispersion is poured thereinto, stored therein for a short while and then discharged at one time, and thereafter the porous element is dried, whereby the filter material of this invention can be obtained. In this invention, such a production process is referred to as paper-making. At this time, if the fibers are short they can be kept even in a deep interior of the porous element, so that is preferable.

It is preferable to further apply a high pressure liquid stream treatment at a pressure of about 3 kg/cm$^2$ to 200 kg/cm$^2$ to the filter material produced by the above-mentioned production process because the fibers can be more uniformly kept in a deeper interior of the porous element in the direction of the thickness thereof.

As a different preferable process for producing the leukocyte-removing filter material of this invention, there is mentioned a process which comprises allowing a microorganism having an ability to produce cellulose fiber and a porous element having an average pore diameter of not less than 1.0 $\mu$m but less than 100 $\mu$m to coexist in a liquid culture medium, culturing the microorganism in the liquid culture medium and thereafter recovering the porous element. Even by this process, there can be produced a leukocyte-removing filter material in which a fiber structure having an average fiber diameter of not less than 0.01 $\mu$m but less than 1.0 $\mu$m are kept on the porous element, the porosity of the filter material is not less than 50% but less than 95%, the keeping proportion of the fiber structure to the above filter material is not less than 0.01% by weight but less than 30% by weight, the ratio between the average pore diameter of the porous element and the average fiber diameter of the fiber structure is not less than 2 but less than 2,000 and the fiber structure forms a reticulate structure. An example of this production process is specifically explained below.

First of all, a porous element as a base material is arranged in a culture medium. The composition of a representative culture medium is 2% of grape sugar, 0.5% of polypeptone, 0.5% of yeast extract, 0.27% of sodium hydrogenphosphate anhydride and 0.115% of citric acid monohydrate. It is sufficient that the porous element is partly contacted with at least the culture medium, and it is preferable that the porous element is arranged in parallel to the surface of the culture medium. A microorganism having an ability to produce cellulose fiber is dispersed in the culture medium so that the microorganism concentration becomes not less than 1 cell/mL but less than $1.0 \times 10^7$ cells/mL. In this state, the microorganism is cultured for a period of 0.5 hour to 48 hours to keep a reticulate fiber structure composed of cellulose fibers on the porous element, thereby producing the leukocyte-removing filter material of this invention. The microorganism having an ability to produce cellulose fiber is inferred to produce cellulose fibers while it wanders in the interior of the porous element, and hence, a reticulate structure of long cellulose fibers is kept in the interior of the porous element in such a state that the fibers are physically and closely entangled. Accordingly, even when the filter material is washed or the leukocyte-containing solution is allowed to flow down in the filter material, the reticulate structure of the cellulose fibers is not broken and does not fall off. Moreover, by controlling the concentration of the microorganism having an ability to produce cellulose fiber in the culture medium, the culturing time and the like, the amount of the cellulose fibers kept on the porous element can be controlled. For example, when the concentration of the microorganism in the culture medium at the time of starting the culture is the same, the keeping proportion is increased by prolonging the culturing time. When the culturing time is the same, the keeping proportion is increased by elevating the concentration of the microorganism in the culture medium at the time of starting the culture.

As the microorganism having an ability to produce cellulose fiber, there can be utilized acetic acid bacteria of the Acetobacter genus, bacteria of the Sarcina genus, bacteria of the Bacterium genus, bacteria of the Agrobacterium genus, bacteria of the Rhizobium genus, bacteria of the Pseudomonas genus, and the like. Among them, acetic acid bacteria of the Acetobacter genus are particularly preferable. The microorganisms of the Acetobacter genus are said to produce fibers having a fiber diameter of 0.01 $\mu$m to 0.1 $\mu$m; however, the use of other microorganisms mentioned above enables the production of fibers having various fiber diameters. When, among the culture medium components, the amounts of the polypeptone which is the nitrogen source and the yeast extract are increased or decreased, the division and proliferation potential of the microorganism can be inhibited, whereby the mesh size of the fiber structure formed can be controlled.

As mentioned hereinbefore, when the microorganism having an ability to produce cellulose fiber is given a vibration during culturing, it cuts the cellulose fibers produced from the bacterial cells in some cases, and hence, in order to keep the reticulate fiber structure on the porous element with a good efficiency in the state that the fibers are physically and closely entangled, it is preferable that the culture is a stationary culture. In addition, when the culture is effected while the liquid level of the liquid culture medium is changed intermittently or continuously to allow the liquid culture medium to pass through the exterior and interior of the porous element, the reticulate fiber structure can be kept in the interior of the porous element with a good efficiency. In general, microorganisms having an ability to produce cellulose fiber are aerobic bacteria and when they are cultured while a gas is fed into the liquid culture medium and/or the interior of the porous element, the ability to produce cellulose fiber is enhanced and the filter material can be produced with a better efficiency. When the microorganisms having an ability to produce cellulose fiber are aerobic bacteria, the existing density of the microorganism tends to become high in the portion in which the dissolved oxygen concentration is relatively high in the neighborhood of the surface of the culture medium. Therefore, in the case of the filter material of this invention produced by carrying out the stationary culture in such a state that the porous element is arranged in parallel to the surface of the culture medium and sunk under the surface of the culture medium, the keeping proportion of the reticulate fiber structure tends to become higher on the upper surface of the porous element. In order to increase the leukocyte-removing performance of the filter material, it is preferable to increase the keeping proportion of the reticulate fiber structure and, for example, it is possible to increase the keeping proportion on the lower surface of the porous element by turning the porous element upside down during the culture.

In order to control the amount of cellulose fibers which can be kept on the porous element by controlling the concentration of the microorganism having an ability to produce cellulose fiber in the culture medium and the culturing time, it is preferable that the microorganism concentration is not less than 1 cell/mL but less than $1.0 \times 10^7$ cells/mL and the culturing time is not less than 0.5 hour but less than 48 hours. When the microorganism concentration is less than 1 cell/mL, the keeping proportion of fibers becomes small in many cases and the leukocyte-removing performance of the filter material becomes low, so that it is not desirable. When the microorganism concentration is not less than $1.0 \times 10^7$ cells/mL, the keeping proportion of the fibers becomes large in many cases and the flow of the leukocyte-containing solution in the filter material becomes bad, so that it is not desirable. As a method of determining the number of microorganism cells having an ability to produce cellulose fiber in the culture medium, a colony counting method can be used. When the culturing time is less than 0.5 hour, the keeping proportion of the reticulate fiber structure is small in many cases, and it is impossible to achieve a high leukocyte-removing performance, so that it is not desirable. When the culturing time is not less than 48 hours, a portion in which the keeping proportion of the reticulate fiber structure is extremely large, namely a skin layer-like structure is formed in many cases on the surface of the porous element and the flow of the leukocyte-containing solution becomes bad, so that it is not desirable.

As a further different process for producing the leukocyte-removing filter material of this invention, there can be mentioned a process for producing a leukocyte-removing filter material in which the reticulate fiber structure is kept on the porous element, the porosity of the filter material is not less than 50% but less than 95%, the keeping proportion of the fiber structure to the filter material is not less than 0.01% by weight but less than 30% by weight and the ratio between the average pore diameter of the porous element and the fiber diameter of the fiber structure is not less than 2 but less than 2,000, which comprises spinning a porous element having an average pore diameter of not less than 1.0 $\mu$m but less than 100 $\mu$m by the melt-blowing process and mixing fibers having an average fiber diameter of not less than 0.01 $\mu$m but less than 1.0 $\mu$m into the fiber bundle stream which is being spun. It is preferable that the leukocyte-removing filter material produced by the above production process is subjected to a high pressure liquid stream treatment at about 3 kg/cm$^2$ to about 200 kg/cm$^2$ because it is made possible to keep the fibers more uniformly and in a deeper interior of the porous element.

The third object of this invention is to provide an apparatus for removing leukocyte which makes it possible to remove the leukocyte from the leukocyte-containing solution while inhibiting the loss of the useful blood components in a very low state and achieve a high leukocyte-removing rate and to provide a process for removing leukocyte using the apparatus as well as to provide an apparatus for removing leukocyte which can achieve a much higher leukocyte-removing rate than conventional apparatus for removing leukocyte and a process for removing leukocyte using the same. The present inventors have made extensive research and have consequently found that the above object can be achieved by filtering a leukocyte-containing solution using a filter apparatus in which the filter material of this invention is appropriately arranged in a vessel having at least a feed opening and a discharging opening.

The filter apparatus for removing leukocyte of this invention is an apparatus in which a filter comprising the filter material of this invention is appropriately packed in a vessel having at least a feed opening and a discharging opening. One filter material layer or plural filter material layers laminated in the flow direction of the leukocyte-containing solution may be packed in the vessel. On the other hand, in the case where a high polymer material-containing solution is poured into a filter material for the purpose of modifying the surface of the filter material to subject the surface to coating treatment or in the like case, the filter material in the lowest layer in the apparatus of this invention sticks onto the internal wall of the apparatus to cause a drift of the leukocyte-containing solution in some cases. In such a case, by inserting a relatively large mesh filter material into the lowest layer, the filter material can be prevented from sticking onto the internal wall of the vessel to cause a drift of the leukocyte-containing solution.

The filter apparatus for removing leukocyte of this invention may further contain other filter materials on the upper stream side and/or the downstream side of the filter material of this invention.

In general, the leukocyte-containing solution contains fine aggregates in many cases. In order to remove leukocyte from a leukocyte-containing solution which contains a large amount of such fine aggregates, a prefilter can be used. As the prefilter, there are preferably used a congregate of fibers having an average fiber diameter of 8 $\mu$m to 50 $\mu$m; an interconnected porous material having an average pore diameter of 20 $\mu$m to 200 $\mu$m; and the like.

It is preferable that the sectional area of the filter material in the normal line direction to the flow direction of the leukocyte-containing solution in the filter apparatus for removing leukocyte of this invention is not less than 3 cm$^2$ but less than 100 cm$^2$. When the sectional area is less than 3 cm$^2$, the flow of the leukocyte-containing solution becomes extremely bad, so that it is not desirable. When the sectional area is not less than 100 cm$^2$, the thickness of the filter has to be made small and a high leukocyte-removing performance cannot be achieved. In addition thereto, the size of the filter apparatus is required to be made large, so that it is not desirable.

The process for removing leukocyte of this invention comprises treating a leukocyte-containing solution in the filter apparatus for removing leukocyte of this invention and recovering the filtered solution. In more detail, it is a process for removing leukocyte from a leukocyte-containing solution which comprises using an apparatus having 1) a feed opening, 2) a filter comprising the filter material of this invention and 3) a discharge opening, pouring a leukocyte-containing solution from the feed opening and recovering the solution filtered through the filter material from the discharge opening.

As the leukocyte-containing solution to be filtered in the filter apparatus for removing leukocyte of this invention, there are mentioned a whole blood preparation, a concentrated erythrocyte preparation, a platelet concentrate preparation and, in addition, a body fluid and the like.

When the leukocyte-containing solution is a whole blood preparation or a concentrated erythrocyte preparation, it is preferable to treat the leukocyte-containing solution in a filter apparatus for removing leukocyte having an apparatus volume of not less than 3 mL but less than 20 mL per one unit. Here, the term "one unit" refers to about 300 mL to 550 ml of a whole blood preparation or a concentrated erythrocyte preparation. When the apparatus volume per one unit is less than 3 mL, the possibility that a high leukocyte-removing rate cannot be achieved is high, so that it is not desirable. When the apparatus volume per one unit is not less than 20 mL, the amount of the useful components in the leukocyte-containing solution remaining unrecovered in the apparatus, in other words, the loss of the useful components becomes large, so that it is not desirable. By filtering the whole blood preparation or the concentrated erythrocyte preparation in the filter apparatus for removing leukocyte of this invention, the leukocyte can be removed until the number of the residual leukocytes in the recovered solution becomes less than $1 \times 10^3$ leukocytes/unit.

When the leukocyte-containing solution is a platelet concentrate preparation, it is preferable to treat the leukocyte-containing solution in a filter apparatus for removing leukocyte having an apparatus volume per 5 units of not less than 1 mL but less than 10 ml. Here, the term "5 units" refers to about 170 mL to about 200 mL of a platelet concentrate preparation. When the apparatus volume per 5 units is less than 1 mL, the possibility that a high leukocyte-removing rate cannot be achieved is high, so that it is not desirable. When the apparatus volume per 5 units is not less than 10 mL, the amount of the useful components remaining unrecovered in the apparatus becomes large, so that it is not desirable. By filtering the platelet concentrate preparation in the filter apparatus for removing leukocyte of this invention, the leukocytes can be removed until the number of the residual leukocytes in the recovered solution becomes less than $1 \times 10^3$ leukocytes/5 units.

When leukocyte is removed using the filter apparatus for removing leukocyte of this invention while the blood transfusion is carried out on the bed side in a hospital, it is preferable to filter the leukocyte-containing solution at a rate of not less than 1 g/min but less than 20 g/min. On the other hand, when leukocyte is removed from a blood preparation for blood transfusion using the filter apparatus for removing leukocyte of this invention in the blood center, it is preferable to filter the leukocyte-containing solution at a rate of not less than 20 g/min but less than 100 g/min.

The filter apparatus for removing leukocyte of this invention can be used for the purpose of not only removing leukocyte, which causes various side effects after the transfusion, from a blood preparation for blood transfusion but also removing leukocyte in the extracorporeal circulation therapy of an autoimmune disease. The extracorporeal circulation therapy of an autoimmune disease comprises continuously filtering the body fluid of a patient, which is the leukocyte-containing solution, in the filter apparatus for removing leukocyte of this invention and returning the recovered solution into the body, thereby removing leukocyte from the body fluid.

As described above, the leukocyte-removing filter material of this invention is very high in affinity with leukocyte, so that it is possible to treat the leukocyte-containing solution with a good efficiency without lowering the treatment rate.

This invention is explained in more detail below based on Examples; however, the scope of this invention should not be construed to be limited to these Examples.

EXAMPLE 1

The preparation of very fine fibers was carried out by the following method. Cuprammonium rayon yarns having a fiber diameter of about 10 $\mu$m (Benberg® yarns of 40 d/45 f manufactured by Asahi Kasei Kogyo K. K.) were used as cleavable fibers and cut to a fiber length of about 3 mm. They were immersed in 3% by weight aqueous sulfuric acid solution and subjected to acid treatment at 70° C. for 30 minutes with slowly stirring at 60 rpm. The sulfuric acid was washed away with pure water and then 1.5 g of the fibers obtained were dispersed in 1 L of pure water and then violently stirred at 10,000 rpm for 30 minutes using a homogenizer to prepare extremely fine fibers.

As a porous element which was the base material, there was used a nonwoven fabric made of a polyester having an average fiber diameter of 1.2 $\mu$m prepared by a melt-blow method and coated with a copolymer composed of 2-hydroxyethyl methacrylate and N,N-dimethylaminoethyl methacrylate (referred to hereinafter as DM) (the DM content in the copolymer was 3 mole %). Speaking in more detail, the above nonwoven fabric made of the polyester was immersed at 40° C. for 1 minute in a 0.2% ethanolic solution of the above copolymer and thereafter the excessive copolymer solution was removed by light squeezing, after which the nonwoven fabric was packed in an exclusive vessel and dried while nitrogen was fed thereinto. The porous diameter had an average pore diameter of 9.2 $\mu$m, a thickness of 0.2 mm, a bulk density of 0.2 g/cm$^3$ and a basis weight of 40 g/m$^2$. The measurement of the average pore diameter was effected using PORE SIZER 9320 (Shimadzu Corp.) in a pressure range of from 1 psia to 2,650 psia, and the average pore diameter was determined to be a fine pore diameter corresponding to an amount of mercury pressurized of 50% obtained under the conditions that the amount of mercury pressurized at a mercury-pressurizing pressure of 1 psia was 0% and the amount of mercury pressurized at a mercury-pressurizing pressure of 650 psia was 100%. The above porous element was cut to a true circle having a diameter of 15 cm and this was arranged on the base of a magnetic funnel having a diameter of 15 cm, after which pure water was stored until a height of about 1 cm from the surface of the porous element. Thereinto was gently poured 50 mL of an aqueous dispersion of the extremely fine fibers (fiber concentration: 0.1 g/L) and slowly stirred. Thereafter, the water was discharged at one time from the base of the magnetic funnel to keep the extremely fine fibers on the porous element, and the fibers were dried under vacuum at 40° C. for 16 hours to obtain a filter material. This operation was repeated twice to prepare a filter material in which extremely fine fibers are kept on both surfaces of the front and back sides of the porous element.

The average fiber diameter of the fiber structure kept on the porous element was 0.29 $\mu$m. The average fiber diameter was determined by taking an electron micrograph of the filter material obtained using a scanning type electron microscope (S-2460N manufactured by Hitachi Ltd.), selecting extremely fine fibers at random, measuring the fiber diameters at 100 or more points and calculating the number average value thereof. Accordingly, the ratio between the average pore diameter of the porous element and the average fiber diameter of the fiber structure became 31.7 and the ratio between the average fiber diameter of the porous element and the average fiber diameter of the fiber structure became 4.1.

Moreover, the porosity of the filter material was 85%, the keeping proportion of the fiber structure to the filter material was 1.1% by weight. The measurement of porosity was as follows: The dry weight ($W_1$ of the filter material cut to a circle of 25 mm in diameter was measured, the thickness thereof was further measured using PEACOK to calculate the volume (V). This filter material was immersed in pure water and subjected to deaeration while irradiated with an ultrasonic wave for about 30 seconds, after which the weight ($W_2$) of the water-containing filter material was measured. From these values, the porosity was determined according to the calculation equation shown below. Incidentally, in the following equation, $\rho$ is the density of pure water and in the present experiment, 1.0 g/cm³ was substituted therefor.

$$\text{Porosity (\%)}=(W_2-W_1)\times\rho\times100/V.$$

The measurement of the keeping proportion of extremely fine fibers was carried out by the method shown below. That is to say, three sheets of a filter material cut to a circle of 25 mm in diameter were immersed in 5 mL of a solution prepared by dissolving 50 mg of cellulase (manufactured by Wako Pure Chemical Industries, Ltd.) in 100 mL of a 0.1 mole/L acetic acid buffer solution (pH: 4.8) and gradually shaken at 50° C. for 24 hours to decompose the extremely fine fibers into glucose which was extracted. The decomposed and extracted glucose was subjected to quantitative determination using glucose CII-TESTWAKO (manufactured by Wako Pure Chemical Industries, Ltd.) which was a glucose determining reagent, and from the amount of glucose, the keeping proportion of the extremely fine fibers introduced into the porous element was calculated.

A laminate (2.6 g) of 7 sheets of the filter material prepared as mentioned above was packed in a vessel having an effective sectional area of filtering portion of 9.0 cm² (3.0 cm×3.0 cm) so that the packing density became 0.21 g/cm³ to prepare a filter apparatus for removing leukocyte. The total volume of the filter material was 1.26 cm³. To 400 mL of blood were added 56 mL of a CPD solution (composition: 26.3 g/L of sodium citrate, 3.27 g/L of citric acid, 23.20 g/L of glucose and 2.51 g/L of sodium hydrogenphosphate dihydrate) to prepare 456 mL of whole blood, and this whole blood was centrifuged and thereafter platelet-rich plasma was removed, after which 95 mL of an MAP solution (composition: 1.50 g/L of sodium citrate, 0.20 g/L of citric acid, 7.21 g/L of glucose, 0.94 g/L of sodium hydrogenphosphate dihydrate, 4.97 g/L of sodium chloride, 0.14 g/L of adenine and 14.57 g/l of mannitol) was added to prepare concentrated erythrocyte (RC-MAP). Fifty grams of the concentrated erythrocyte (RC-MAP, hematocrit: 64%, number of erythrocytes: 3,425 cells/$\mu$L) which had been stored at 4° C. for 8 days was filtered through the above-mentioned filter apparatus for removing leukocyte. The temperature of the concentrated erythrocyte just before the starting of filtration was 10° C. The filtration of the concentrated erythrocyte in the above filter apparatus was carried out at a falling distance of 1.0 m until the presence of the concentrated erythrocyte in the blood bag became not confirmed, to recover the blood (the recovered concentrated erythrocyte is referred to hereinafter as the recovered liquid). The average treating rate in the filtration of the concentrated erythrocyte was 11.6 g/min.

The volumes of the concentrated erythrocyte before filtration (referred to hereinafter as the liquid before filtration) and the recovered liquid and the number of leukocytes were measured and the proportion of the residual leukocyte was determined.

Proportion of the residual leukocyte=(number of leukocytes in the recovered liquid)/(number of leukocytes in the liquid before filtration)

Incidentally, the volumes of the liquid before filtration and the recovered liquid were values obtained by dividing the respective weights by the specific gravity of the blood preparation (1.075). The leukocyte concentration in the liquid before filtration was measured by injecting the liquid before filtration diluted 10 times with a Turk's reagent into a Bürker-Türk hemocytometer and counting the number of leukocytes using an optical microscope. Also, the measurement of the leukocyte concentration in the recovered liquid was carried out by the method shown below. The recovered liquid was diluted to 5 times with a LEUCOPLATE solution (manufactured by SOBIODA Company). The diluted liquid was well mixed and thereafter allowed to stand at room temperature for 6 to 10 minutes. This was centrifuged at 2,750×g for 6 minutes and the supernatant was removed to adjust the amount of the liquid to 1.02 g. This sample liquid was well mixed and thereafter injected into a Nageotte hemocytometer and counting the number of leukocytes using an optical microscope, thereby determining the leukocyte concentration. From the above results, it was found that the proportion of the residual leukocyte was $10^{-2.71}$.

COMPARATIVE EXAMPLE 1

A laminate (0.29 g) of 8 sheets of only the same porous element as sued in Example 1 (average fiber diameter: 1.2 $\mu$m, average pore diameter: 9.2 $\mu$m) was packed in a vessel having an effective sectional area of filtering portion of 9.0 cm² (3.0 cm×3.0 cm) so that the packing density became 0.20 g/cm³ to prepare a filter apparatus for removing leukocyte. The porosity of the above porous element was 86% and the volume thereof was 1.44 cm³. Using this filter apparatus, 50 g of the same concentrated erythrocyte liquid as in Example 1 was filtered in the same manner as in Example 1. The temperature of the concentrated erythrocyte just before the starting of filtration was 10° C. From the above results, it was found that the average treating rate was 13.2 g/min and the proportion of the residual leukocyte was $10^{-1.18}$.

COMPARATIVE EXAMPLE 2

A nonwoven fabric made of polyethylene having an average fiber diameter of 0.6 $\mu$m prepared by a flash-spinning process was freeze-crushed using a liquefied nitrogen to obtain a small fiber mass having a longer diameter of less than 1 mm. In 5 L of a 1% by weight ethanolic Tween® 20 solution were dispersed 0.1 g of the above small fiber mass and 1.5 g of fibers prepared by cutting long fibers made of a polyester having an average fiber diameter of 7.2 $\mu$m to a 5-mm fiber length. This dispersion was poured into a magnetic funnel, on the base of which a mesh of an open pore diameter of 200 $\mu$m was arranged, and then the ethanol was at one time discharged to obtain a filter having a basis weight of 50 g/m².

Figure 3:
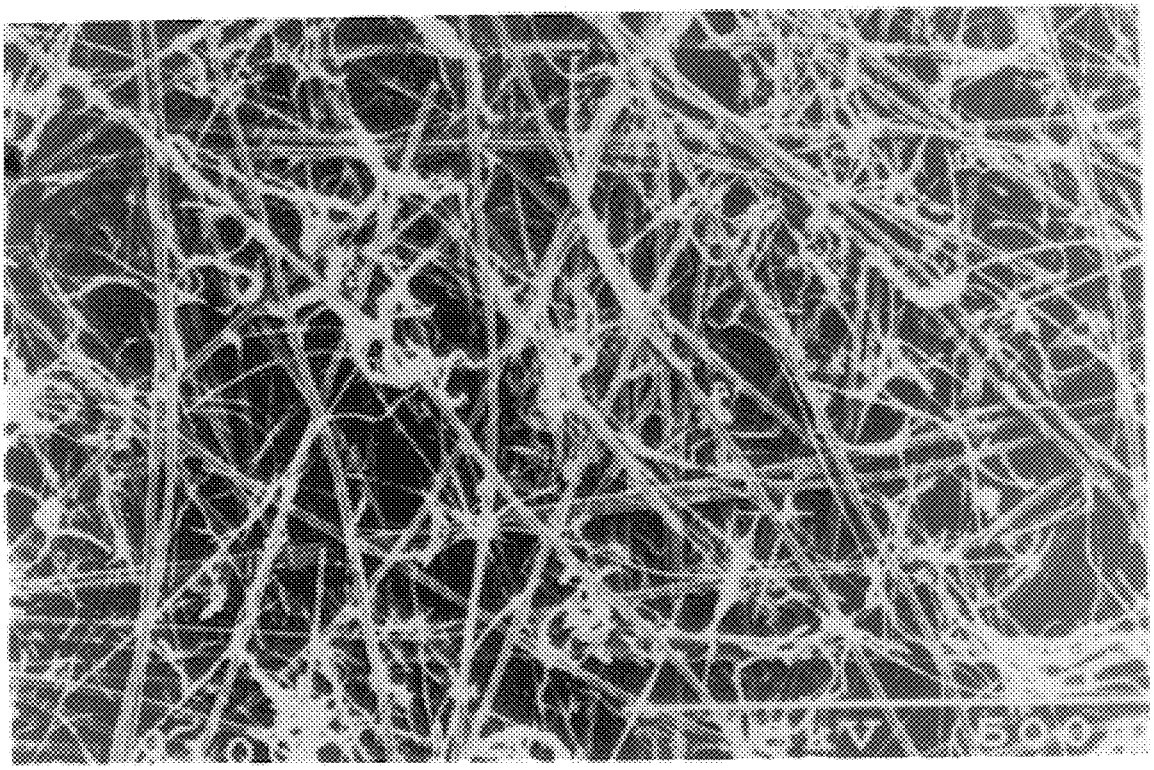
FIG. 3 is an electron micrograph of a nonwoven fabric filter material in which fibers having different fiber diameters are mixed and entangled.

LeukoNet® which was a leukocyte-removing filter manufactured by HEMASURE Company was disjointed and a filter material was taken out. This filter material was a nonwoven fabric-like filter material made of a mixture of fibers having different fiber diameters in which the average fiber diameter of the extremely fine fibers was 0.5 $\mu$m; the average fiber diameter of the base material was 7.8 $\mu$m; the ratio between the average fiber diameter of the base material and the average fiber diameter of the extremely fine fiber was 15.6; and the porosity of the filter material was 92%. As a result of observation through an electron microscope, the above-mentioned two kinds of filter materials were similar in structure and both did not form a reticulate structure. An electron micrograph of the latter filter material is shown in FIG. 3. Among the above two kinds of filter materials, one sheet (0.20 g) of the latter filter material was packed in a vessel having an effective sectional area of filtering portion of 9.0 cm³ (3.0 cm×3.0 cm) so that the packing density became 0.13 g/cm³ to prepare a leukocyte-removing filter material. The total volume of the filter material was 1.53 cm³. Using this filter apparatus, 50 g of the same concentrated erythrocyte as in Example 1 was filtered in the same manner as in Example 1. The temperature of the concentrated erythrocyte just before the filtration was 10° C. From the above results, it was found that the average treating rate was 9.5 g/min and the proportion of the residual leukocyte was $10^{-0.68}$.

Example 1, Comparative Example 1 and Comparative Example 2 are comparisons of the effect of introducing fibers having an average fiber diameter of not less than 0.01 μm but less than 1.0 μm and the effect of reticulate structure of the said fibers. Also, it is often observed in the case of the conventional fiber-like leukocyte-removing filter material that leukocytes are captured in the state that they contact with the fibers at about 1 to 3 points; however, it is relatively often observed in the case of the filter material of this invention that leukocytes are captured in the state that they contact with the fibers at so many points as 3 or more points.

EXAMPLE 2

The above fibers prepared in the same manner as in Example 1 were kept in the same manner as in Example 1 on the same porous element as used in Example 1 to prepare a filter material in which extremely fine fibers were kept on both surfaces on the front and back sides of the porous element. The extremely fine fibers kept had an average fiber diameter of 0.25 μm; the ratio between the average pore diameter of the porous element and the average fiber diameter of the extremely fine fibers was 36.8; the ratio between the average fiber diameter of the porous element and the average fiber diameter of the extremely fine fibers was 4.8; the porosity of the filter material was 85% and the keeping proportion of the fiber structure to the filter material was 1.3% by weight. A laminate (0.26 g) of 7 sheets of this filter material was packed in a vessel having an effective sectional area of filtering portion of 9.0 cm² (3.0 cm×3.0 cm) so that the packing density became 0.21 g/cm³ to prepare a filter apparatus for removing leukocyte. The total volume of the filter material was 1.26 cm³. Using this filter apparatus, 50 g of concentrated erythrocyte (RC-MAP, hematocrit: 62%, number of leukocytes: 3,785 cells/μL) which had been stored at 4° C. for 7 days, was filtered in the same manner as in Example 1. The temperature of the concentrated erythrocyte just before the starting of filtration was 10° C. From the above results, it was found that the average treating rate was 10.2 g/min and the proportion of the residual leukocyte was $10^{-2.97}$.

EXAMPLE 3

The same porous element as used in Example 1 was cut to a size of 25 cm×35 cm, immersed in 375 mL of a culture medium having an acetic acid bacterium concentration of 164 cells/mL and subjected in this state to stationary culture at 28° C. for 14 hours. During the stationary culture, the porous element was turned upside down every two hours. After completion of the stationary culture, washing with a water stream was effected to remove the acetic acid bacteria. According to the above-mentioned production process, there was obtained a filter material in which a reticulate structure composed of cellulose fibers produced by the acetic acid bacterium having an average fiber diameter of 0.02 μm were kept on the surfaces of the front and back sides of the porous element. As the acetic acid bacterium, there was used Acetobacter xylinum IFO13693). The composition of the culture medium was 2% of grape sugar, 0.5% of polypeptone, 0.5% of yeast extract, 0.27% of sodium hydrogenphosphate anhydride and 0.115% of citric acid monohydrate. As a method of determining the number of bacterial cells in the culture medium, a colony counting method was used. That is to say, a suspension of the acetic acid bacterium in the culture medium was diluted and a given amount thereof was sampled. This was mixed with a culture medium containing 0.75% of agar, then poured onto a petri dish and cooled for a short period of time to be solidified. Thereto was further added a given amount of a culture medium containing 0.75% of agar, and the culturing was continued for at least 4 days and the number of colonies formed out of acetic acid bactera's cells was counted, thereby determining the number of bacterial cells. As a result of observation through an electron microscope, this filter material formed a reticulate structure. The average fiber diameter of the fiber structure was 0.02 μm, the ratio between the average pore diameter of the porous element to the average fiber diameter of the fiber structure was 460, the ratio between the average fiber diameter of the porous element and the average fiber diameter of the fiber structure was 60, the porosity of the filter material was 85% and the keeping proportion of the fiber structure to the filter material was 0.05% by weight.

0.26 g of this filter material was packed in a vessel having an effective sectional area of filtering portion of 9.0 cm² (3.0 cm×3.0 cm) so that the packing density became 0.21 g/cm³ to prepare a filter apparatus for removing leukocyte. The total volume of the filter material was 1.26 cm³. Using this filter apparatus, 50 g of the same concentrated erythrocyte as in Example 2 (RC-MAP, hematocrit: 62%, number of leukocytes: 3,785 cells/μL) was filtered in the same manner as in Example 1. The temperature of the concentrated erythrocyte just before the starting of filtration was 10° C. From the above results, it was found that the average treating rate was 12.4 g/min and the proportion of the residual leukocyte was $10^{-2.80}$.

EXAMPLE 4

To a high pressure liquid treatment was subjected a filter material in which the extremely fine fibers were kept on both surfaces of the front and back sides of a porous element which filter material had been obtained by subjecting to the same operation as in Example 1 the same porous element as used in Example 1 and extremely fine fibers prepared by cutting cuprammonium rayon yarn (Benberg® yarn of 40 d/45 f manufactured by Asahi Kasei Kogyo K. K.) having a fiber diameter of about 10 μm so that the fiber length became about 0.8 mm and subjecting the fibers to the same operation as in Example 1. That is to say, the above filter material was subjected to columnar stream treatment (15 kg/cm²) under the conditions that the nozzle diameter was 0.2 mm, the nozzle pitch was 5 mm, the number of nozzle lines was 18, the distance between web and nozzle was 30 mm, the number of revolutions of nozzle header was 150 rpm and the moving speed of filter material was 5 m/min to prepare a filter material. As a result of observation through an electron microscope, this filter material formed a reticulate structure. The average fiber diameter of the extremely fine fibers was 0.23 μm, the ratio between the average pore diameter of the porous element and the average fiber diameter of the extremely fine fibers was 40.0, the ratio between the average fiber diameter of the porous element and the average fiber diameter of the extremely fine fibers was 5.2, the porosity of the filter material was 82% and the keeping proportion of the fiber structure to the filter material was 10.3% by weight.

0.33 g of this filter material was packed in a vessel having an effective sectional area of filtering portion of 9.0 cm² (3.0 cm×3.0 cm) so that the packing density became 0.26 g/cm³ to prepare a filter apparatus for removing leukocyte. The total volume of the filter material was 1.26 cm³. Using this filter apparatus, the same concentrated erythrocyte as in Example 2 (RC-MAP, hematocrit: 62%, number of leukocytes: 3,785 cells/μL) was filtered in the same manner as in Example 1. The temperature of the concentrated erythrocyte just before the starting of filtration was 10° C. From the above results, it was found that the average treating speed was 6.7 g/min and the proportion of the residual leukocyte was $10^{-3.10}$.

COMPARATIVE EXAMPLE 3

The same porous element as used in Example 1 was cut to a size of 25 cm×35 cm, immersed in 375 mL of a culture medium having an acetic acid bacterium concentration of 164 cells/mL and subjected in this state to stationary culture at 28° C. for 2 hours. After completion of the stationary culture, washing with a water stream was effected to remove the acetic acid bacterium. By the above-mentioned production process, there was obtained a filter material in which a reticulate structure composed of cellulose fibers produced by the acetic acid bacterium having an average fiber diameter of 0.02 μm were kept on the surface of one side of the porous element. The acetic acid bacterium used and the composition of the culture medium were the same as in Example 3. The average fiber diameter of the extremely fine fiber structure was 0.02 μm, the ratio between the average pore diameter of the porous element to the average fiber diameter of the extremely fine fiber structure was 460, the ratio between the average fiber diameter of the porous element and the average fiber diameter of the extremely fine fiber structure was 60, the porosity of the filter material was 85% and the keeping proportion of the extremely fine fiber structure to the filter material was 0.005% by weight.

0.26 g of this filter material was packed in a vessel having an effective sectional area of filtering portion of 9.0 cm² (3.0 cm×3.0 cm) so that the packing density became 0.21 g/cm³ to prepare a filter apparatus for removing leukocyte. The volume of the filter material was 1.26 cm³. Using this filter apparatus, 50 g of the same concentrated erythrocyte as in Example 2 (RC-MAP, hematocrit: 62%, number of leukocytes: 3,785 cells/μL) was filtered in the same manner as in Example 1. The temperature of the concentrated erythrocyte just before the staring of filtration was 10° C. From the above results, it was found that the average treating rate was 10.2 g/min and the proportion of the residual leukocyte was $10^{-1.67}$.

COMPARATIVE EXAMPLE 4

Extremely fine fibers prepared in the same manner as in Example 1 and the same porous element as used in Example 1 were subjected to the same operation as in Example 1 to obtain a filter material in which the extremely fine fibers were kept on both surfaces of the front and back sides of the porous element. Such a filter material was prepared that the average fiber diameter of the extremely fine fibers was 0.25 μm, the ratio between the average pore diameter of the porous element and the average fiber diameter of the extremely fine fiber structure was 36.8, the ratio between the average fiber diameter of the porous element and the average fiber diameter of the extremely fine structure was 4.8, the porosity of the filter material was 48% and the keeping proportion of the fiber structure to the filter material was 59% by weight.

0.91 g of this filter material was packed in a vessel having an effective sectional area of filtering portion of 9.0 cm² (3.0 cm×3.0 cm) so that the packing density became 0.72 g/cm³ to prepare a filter apparatus for removing leukocyte. The total volume of the filter material was 1.26 cm³. Using this filter apparatus, 50 g of concentrated erythrocyte (RC-MAP, hematocrit: 62%, number of leukocytes: 3,785 cells/μL) was filtered in the same manner as in Example 1. However, the filter material caused clogging soon and the concentrated erythrocyte did not flow at all. The temperature of the concentrated erythrocyte just before the starting of filtration was 10° C.

COMPARATIVE EXAMPLE 5

Cuprammonium rayon yarn (Benberg® yarn of 40 d/45 f manufactured by Asahi Kasei Kogyo K. K.) having a fiber diameter of about 10 μm was cut so that the fiber length became about 5 mm and extremely fine fibers were prepared according to the operation of Example 1. The treatment in a homogenizer was effected at 10,000 rpm for 5 minutes. Using the extremely fine fibers prepared, a nonwoven fabric made of a polyester having an average fiber diameter of 1.2 μm and an average pore diameter of 1.6 μm prepared by a melt-blow method, as a porous element, was subjected to coating treatment using a 0.2% ethanolic solution of a copolymer consisting of 2-hydroxyethyl methacrylate and N,N-dimethylaminoethyl methacrylate (the DM content in the copolymer was 3 mole %) in the same manner as in Example 1, and then to heat-compression at 110° C. Using this porous element, a filter material in which the extremely fine fibers were kept on both surfaces of the front and back sides of the porous element was obtained in the same manner as in Example 1. The fiber structure kept on the porous element formed a reticulate structure. Such a filter material was prepared that the average fiber diameter of the fiber structure was 0.93 μm, the ratio between the average pore diameter of the porous element and the average fiber diameter of the fiber structure was 1.7, the ratio between the average fiber diameter of the porous element and the average fiber diameter of the fiber structure was 1.3, the porosity of the filter material was 55% and the keeping proportion of the fiber structure to the filter material was 1.3% by weight.

0.78 g of this filter material was packed in a vessel having an effective sectional area of filtering portion of 9.0 cm² (3.0 cm ×3.0 cm) so that the packing density became 0.62 g/cm³ to prepare a filter apparatus for removing leukocyte. The total volume of the filter material was 1.26 cm³. Using this filter apparatus, 50 g of concentrated erythrocyte (RC-MAP, hematocrit: 62%, number of leukocytes: 3,785 cells/μL) was filtered in the same manner as in Example 1. However, the filter material caused clogging soon and the concentrated erythrocyte did not flow at all. The temperature of the concentrated erythrocyte just before the starting of filtration was 10° C.

COMPARATIVE EXAMPLE 6

A porous element prepared by subjecting a spunbonded nonwoven fabric made of a polyester having an average fiber diameter of 25 μm and an average pore diameter of 85 μm to coating treatment with a 0.2% ethanolic solution of a copolymer consisting of 2-hydroxyethyl methacrylate and N,N-dimethylaminoethyl methacrylate (DM) (the DM content in the copolymer was 3 mole %) in the same manner as in Example 1, was cut to a size of 25 cm×35 cm, immersed in 375 mL of a culture medium having an acetic acid bacterium concentration of 112 cells/mL, and subjected in this state to stationary culture at 28° C. for 10 hours. During the stationary culture, the porous element was turned upside down every 2 hours. After completion of the stationary culture, washing with a water stream was effected to remove the acetic acid bacterium. According to the above production process, there was obtained a filter material in which a fiber structure composed of cellulose fibers having an average fiber diameter of 0.02 μm produced by the acetic acid bacterium was kept on the surfaces of the front and back sides of the porous element. The acetic acid bacterium used and the composition of the culture medium used were the same as in Example 3. The average fiber diameter of the fiber structure was 0.02 μm, the ratio between the average pore diameter of the porous element and the average fiber diameter of the fiber structure was 4,250, the ratio between the average fiber diameter of the porous element and the average fiber diameter of the fiber structure was 1,250, the porosity of the porous element was 85% and the keeping proportion of the fiber structure to the filter material was 0.01% by weight.

0.26 g of this filter material was packed in a vessel having an effective sectional area of filtering portion of 9.0 cm$^2$ (3.0 cm×3.0 cm) so that the packing density became 0.21 g/cm$^3$ to prepare a filter apparatus for removing leukocyte. The total volume of the filter material was 1.26 cm$^3$. Using this filter apparatus, in the same manner as in Example 1, 50 g of the same concentrated erythrocyte as in Example 2 (RC-MAP, hematocrit: 62%, number of leukocytes: 3,785 cells/μL) was filtered. The temperature of the concentrated erythrocyte just before the starting of filtration was 10° C. From the above results, it was found that the average treating rate was 25.2 g/min and the proportion of the residual leukocyte was $10^{-0.08}$.

Examples 2 to 4 and Comparative Examples 3 to 6 are comparisons of the keeping proportion of fibers having an average fiber diameter of not less than 0.01 μm but less than 1.0 μm to the filter material, the ratio between the average pore diameter of the porous element and the average fiber diameter of the fiber structure, or the ratio between the average fiber diameter of the porous element and the average fiber diameter of the fiber structure.

EXAMPLE 5

Extremely fine fibers prepared in the same manner as in Example 1 and a continuous porous element made of a polyurethane having an average pore diameter of 7.6 μm as the porous element were subjected to the same operation as in Example 1 to obtain a filter material in which the extremely fine fibers were kept on both surfaces on the front and back sides of the porous element. The extremely fine fibers had an average fiber diameter of 0.25 μm, the ratio between the average pore diameter of the porous element and the average fiber diameter of the fiber structure was 30.4, the porosity of the filter material was 87% and the keeping proportion of the fiber structure to the filter material was 1.3% by weight.

0.23 g of this filter material was packed in a vessel having an effective sectional area of filtering portion of 9.0 cm$^2$ (3.0 cm×3.0 cm) so that the packing density became 0.21 g/cm$^3$ to prepare a filter apparatus for removing leukocyte. The total volume of the filter material was 1.08 cm$^3$. Using this filter apparatus, 50 g of concentrated erythrocyte (RC-MAP, hematocrit: 62%, number of leukocytes: 4,125 cells/μL) which had been stored at 4° C. for 8 days was filtered in the same manner as in Example 1. The temperature of the concentrated erythrocyte just before the starting of filtration was 10° C. From the above results, it was found that the average treating rate was 14.6 g/min and the proportion of the residual leukocyte was $10^{-2.83}$.

EXAMPLE 6

The same porous element as used in Example 1 was cut to a size of 25 cm×35 cm, immersed in 375 mL of a culture medium having an acetic acid bacterium concentration of 183 cells/mL and subjected in this state to stationary culture at 28° C. for 14 hours. During the stationary culture, the porous element was turned upside down every two hours. After completion of the stationary culture, washing with a water stream was effected to remove the acetic acid bacterium. According to the above-mentioned production process, there was obtained a filter material in which a reticulate fiber structure composed of cellulose fibers produced by the acetic acid bacterium having an average fiber diameter of 0.02 μm were kept on the surfaces on the front and back sides of the porous element. The acetic acid bacterium used and the composition of the culture medium used were the same as in Example 3. The average fiber diameter of the fiber structure was 0.02 μm, the ratio between the average pore diameter of the porous element and the average fiber diameter of the fiber structure was 460, the ratio between the average fiber diameter of the porous element and the average fiber diameter of the fiber structure was 60, the porosity of the filter material was 85% and the keeping proportion of the fiber structure to the filter material was 0.06% by weight.

0.30 g of this filter material was packed in a vessel having an effective sectional area of filtering portion of 9.0 cm$^2$ (3.0 cm×3.0 cm) so that the packing density became 0.21 g/cm$^3$ to prepare a filter apparatus for removing leukocyte. The total volume of the filter material was 1.44 cm$^3$. Using this filter apparatus, 50 g of the same concentrated erythrocyte as in Example 5 (RC-MAP, hematocrit: 62%, number of leukocytes: 4,125 cells/μL) was filtered in the same manner as in Example 1. The temperature of the concentrated erythrocyte just before the starting of filtration was 10° C. From the above results, it was found that the average treating rate was 11.2 g/min and the proportion of the residual leukocyte was $10^{-2.92}$.

COMPARATIVE EXAMPLE 7

The same porous element as used in Example 1 was cut to a size of 25 cm×35 cm, immersed in 500 mL of a culture medium having an acetic acid bacterium concentration of 465 cells/mL and subjected in this state to stationary culture at 28° C. for 10 hours. After completion of the stationary culture, washing with a water stream was effected to remove the acetic acid bacterium. According to the above-mentioned production process, there was obtained a filter material which was a composite of the porous element with the bacterial cellulose membrane. The acetic acid bacterium used and the composition of the culture medium used were the same as in Example 3. The average fiber diameter of the fibers forming the bacterial cellulose membrane was 0.02 μm, the ratio between the average pore diameter of the porous element to the average fiber diameter of the fiber structure was 460, the ratio between the average fiber diameter of the porous element and the average fiber diameter of the fiber structure was 60, the porosity of the filter material was 85% and the keeping proportion of the fiber structure to the filter material was 50.3% by weight.

0.67 g of this filter material was packed in a vessel having an effective sectional area of filtering portion of 9.0 cm² (3.0 cm×3.0 cm) so that the packing density became 0.40 g/cm³ to prepare a filter apparatus for removing leukocyte. The total volume of the filter material was 1.68 cm³. Using this filter apparatus, 50 g of the same concentrated erythrocyte as in Example 5 (RC-MAP, hematocrit: 62%, number of leukocytes: 4,125 cells/μL) was filtered in the same manner as in Example 1. However, the filter material caused clogging soon and the concentrated erythrocyte did not flow at all. The temperature of the concentrated erythrocyte just before the starting of filtration was 10° C.

EXAMPLE 7

To the same operation as in Example 1 were subjected extremely fine fibers prepared in the same manner as in Example 1 and a nonwoven fabric made of a polyester having an average fiber diameter of 1.2 μm and an average pore diameter of 9.2 μm prepared by a melt-blow method to obtain a filter material in which the extremely fine fibers were kept on both surfaces on the front and back sides of a porous element. The average fiber diameter of the extremely fine fibers was 0.29 μm, the ratio between the average pore diameter of the porous element and the average fiber diameter of the fiber structure was 31.7, the ratio between the average fiber diameter of the porous element and the average fiber diameter of the fiber structure was 4.1, the porosity of the filter material was 85% and the keeping proportion of the fiber structure to the filter material was 1.2% by weight.

On the upper stream side of 1.8 g of this filter material were arranged 0.63 g of a nonwoven fabric made of a polyester having an average fiber diameter of 19 μm and a basis weight of 70 g/m², 0.27 g of a nonwoven fabric made of a polyester having an average fiber diameter of 12 μm and a basis weight of 30 g/m² and 0.59 g of a nonwoven fabric made of a polyester having an average fiber diameter of 1.7 μm and a basis weight of 66 g/m², and they were packed in a vessel having an effective sectional area of filtering portion of 45 cm² (6.7 cm×6.7 cm) so that the packing density became 0.23 g/cm³. Into this vessel was poured at a flow rate of 80 g/min a 0.2% ethanolic solution of a copolymer consisting of 2-hydroxyethyl methacrylate and N,N-dimethylaminoethyl methacrylate (DM) (the DM content in the copolymer was 3 mole %) while the ethanolic solution was maintained at 40° C., and then recycled for 1.5 hours, after which nitrogen was introduced into the vessel at a flow rate of 1.5 L/min to remove the excessive coating solution. Vacuum drying was further effected at 60° C. for 16 hours to prepare a filter apparatus for removing leukocyte.

Using this filter apparatus, 515 g of CPD-added fresh human whole blood (hematocrit: 39%, number of leukocytes: 4,865 cells/μL) was filtered. The temperature of the CPD-added fresh human whole blood just before the starting of filtration was 25° C. When the filtration was started, the filter apparatus was connected to a blood bag containing the CPD-added fresh human whole blood through the blood circuit, and thereafter, a pressure of 100 mmHg was applied to the blood bag using a pressuring cuff to forcibly fill the filter apparatus with the CPD-added fresh human whole blood. After the filter apparatus had been filled with the CPD-added fresh human whole blood as mentioned above, the CPD-added fresh human whole blood was treated at a falling distance of 0.7 m and the filtration was carried out until the presence of the CPD-added fresh human whole blood in the blood bag was not been confirmed, and the filtered blood was recovered. From the above results, it was found that the average treating rate was 29.6 g/min, the proportion of the residual leukocyte was $10^{-3.99}$ and the recovery of erythrocyte was 93.8%.

COMPARATIVE EXAMPLE 8

In Example 7, 5.78 g of a nonwoven fabric made of a polyester having an average fiber diameter of 1.2 μm and an average pore diameter of 9.3 μm prepared by a melt-blow method was packed in place of the filter material of this invention and subjected to the same coating treatment as in Example 7 to prepare a filter apparatus. Incidentally, the packing density was adjusted to 0.26 g/cm³.

Using this filter apparatus, the same CPD-added fresh human whole blood as in Example 7 was treated in the same manner as in Example 7. As a result, it was found that the average treating rate was 24.8 g/min, the proportion of the residual leukocyte was $10^{-3.91}$ and the recovery of erythrocyte was 89.6%.

Though the amount of the filter material in the filter apparatus in Example 7 was about ⅓ of the amount of the main filter material (filter material having an average fiber diameter of 1.2 μm) in the filter apparatus in Comparative Example 8, it can be seen that the leukocyte-removing performance and the average treating rate were at least equivalent and the loss of erythrocyte was reduced about 40%.

EXAMPLE 8

On the upper stream side of 1.3 g of the same filter material of this invention as in Example 7 were arranged 1.35 g of a nonwoven fabric made of a polyester having an average fiber diameter of 33 μm and a basis weight of 50 g/m², 0.81 g of a nonwoven fabric made of a polyester having an average fiber diameter of 12 μm and a basis weight of 30 g/m² and 0.59 g of a nonwoven fabric made of a polyester having an average fiber diameter of 1.7 μm and a basis weight of 66 g/m², and they were packed in a vessel having an effective sectional area of filtering portion of 45 cm² (6.7 cm×6.7 cm) so that the packing density became 0.22 g/cm³ and then subjected to the same coating treatment as in Example 7 to prepare a filter apparatus.

Using this filter apparatus, 325 g of concentrated erythrocyte (RC-MAP, hematocrit: 64%, number of leukocytes: 5,260 cells/μL) which had been stored at 4° C. for 10 days was filtered in the same manner as in Example 7 at a falling distance of 1.0 m. The temperature of the concentrated erythrocyte just before the starting of filtration was 12° C. From the above results, it was found that the average treating rate was 17.6 g/min, the proportion of the residual leukocyte was $10^{-4.02}$ and the recovery of erythrocyte was 94.3%.

COMPARATIVE EXAMPLE 9

In Example 8, a nonwoven fabric made of a polyester having an average fiber diameter of 1.2 μm and an average pore diameter of 9.3 μm prepared by a melt-blow method was packed in place of the filter material of this invention and subjected to the same coating treatment as in Example 7 to prepare a filter apparatus. Incidentally, the packing density was adjusted to 0.22 g/cm³.

Using this filter apparatus, 325 g of the same concentrated erythrocyte as in Example 8 (RC-MAP, hematocrit: 64%, number of leukocytes: 5,260 cells/μL) was filtered in the same manner as in Example 8 at a falling distance of 1.0 m. As a result, it was found that the average treating rate was 19.5 g/min, the proportion of the residual leukocyte was $10^{-3.94}$, and the recovery of erythrocyte was 89.2%.

Though the amount of the filter material in the filter apparatus in Example 8 was about ⅓ of that of the main filter material (filter material having an average fiber diameter of 1.2 μm) in the filter apparatus of Comparative Example 9, it can be seen that the leukocyte-removing performance and the average treating rate in the filter apparatus of Example 8 were at least equivalent and in addition, the loss of erythrocyte was reduced about 50%.

EXAMPLE 9

On the upper stream side of 0.32 g of the same filter material of this invention as in Example 7 were arranged 0.13 g of a nonwoven fabric made of a polyester having an average fiber diameter of 19 μm and a basis weight of 70 g/m² and 0.11 g of a nonwoven fabric made of a polyester having an average fiber diameter of 2.3 μm and a basis weight of 60 g/m², and they were packed in a vessel having an effective sectional area of filtering portion of 9 cm² (3.0 cm×3.0 cm) so that the packing density became 0.21 g/cm³. Into this vessel was poured at a flow rate of 80 g/min a 1.0% ethanolic solution of a copolymer composed of 2-hydroxyethyl methacrylate and N,N-dimethylaminoethyl methacrylate (DM) (the DM content in the copolymer was 3 mole %) while the ethanolic solution was maintained at 40° C., and recycled for 1.5 minutes, after which nitrogen was introduced at a flow rate of 1.5 L/min into the vessel to remove the excessive coating solution. In addition, by effecting vacuum drying at 40° C. for 16 hours, a filter apparatus for removing leukocyte was prepared.

Using this filter apparatus, 400 g of platelet concentrate (number of platelets: 9.9×10⁵ cells/μL, number of leukocytes: 1,075 cells/μL) which had been stored at room temperature for 4 days with gentle shaking was filtered. The temperature of the platelet concentrate just before the starting of filtration was 23° C. The platelet concentrate was treated at a falling distance of 1.0 m and the filtration was effected until the presence of the platelet concentrate in the blood bag was not confirmed, and the filtered blood was recovered. The leukocyte concentration of the liquid before filtration was determined by injecting the liquid before filtration diluted 10 times with a Türk's reagent into a Bürker-Türk type hemocytometer and counting the number of leukocytes through an optical microscope to determine the leukocyte concentration. The leukocyte concentration in the recovered liquid was determined by concentrating the recovered liquid to 10 times or 20 times by a centrifugal operation (800 G×10 minutes), dyeing the leukocytes with an acridine orange solution and then counting them using a Neubauer hemocytometer. The platelet concentration was measured by an automatic hemocytometer Sysmex K-4500 (manufactured by Toa Iyo Denshi K. K.). From the above results, it was found that the average treating rate was 27.3 g/min, the proportion of the residual leukocyte was $10^{-3.73}$ and the recovery of platelet was 93.7%.

COMPARATIVE EXAMPLE 10

In Example 9, a nonwoven fabric made of a polyester having an average fiber diameter of 1.2 μm and an average pore diameter of 9.3 μm prepared by a melt-blow method was packed in place of the filter material of this invention, and subjected to the same coating treatment as in Example 9 to prepare a filter apparatus. Incidentally, the packing density was adjusted to 0.23 g/cm³.

Using this filter apparatus, the same platelet concentrate as in Example 9 was treated in the same manner as in Example 9. As a result, it was found that the average treating rate was 30.1 g/min, the proportion of the residual leukocyte was $10^{-3.38}$ and the recovery of platelet was 85.4%.

Though the amount of the main filter material in the filter apparatus in Example 9 was about ⅓ of the amount of the main filter material (filter material having an average fiber diameter of less than 1.2 μm) in the filter apparatus in Comparative Example 10, it can be seen that the leukocyte-removing performance and the average treating rate in the filter apparatus in Example 9 were at least equivalent, and in addition, the loss of the platelet was reduced about 55%.

EXAMPLE 10

Extremely fine fibers prepared in the same manner as in Example 1 and a nonwoven fabric made of a polyester having an average fiber diameter of 1.2 μm and an average pore diameter of 9.2 μm prepared by a melt-blow method were subjected to the same operation as in Example 1 to prepare a filter material kept on both surfaces on the front and back sides of the porous element. The average fiber diameter of the extremely fine fibers was 0.19 μm, the ratio between the average pore diameter of the porous element and the average fiber diameter of the fiber structure was 48.4, the ratio between the average fiber diameter of the porous element and the average fiber diameter of the fiber structure was 6.3, the porosity of the filter material was 85% and the keeping proportion of the fiber structure to the filter material was 1.4% by weight.

On the upper stream side of 3.96 g of this filter material were arranged 1.35 g of a nonwoven fabric made of a polyester having an average fiber diameter of 33 μm and a basis weight of 50 g/m², 0.81 g of a nonwoven fabric made of a polyester having an average fiber diameter of 12 μm and a basis weight of 30 g/m² and 0.59 g of a nonwoven fabric made of a polyester having an average fiber diameter of 1.7 μm and a basis weight of 66 g/m², and they were packed in a vessel having an effective sectional area of filtering portion of 45 cm² (6.7 cm×6.7 cm) so that the packing density became 0.22 g/cm³. Subsequently, by applying the same coating treatment as in Example 7, a filter apparatus for removing leukocyte was prepared.

Using this filter apparatus, 325 g of concentrated erythrocyte (RC-MAP, hematocrit: 63%, number of leukocytes: 4,935 cells/μL) which had been stored at 4° C. for 7 days, was filtered. The temperature of the concentrated erythrocyte just before the starting of filtration was 12° C. When the filtration was started, the filter apparatus was connected to a blood bag containing the concentrated erythrocyte through the blood circuit, and thereafter, a pressure of 100 mmHg was applied to the blood bag using a pressuring cuff to forcibly fill the filter apparatus with the concentrated erythrocyte. After the filter apparatus had been filled with the concentrated erythrocyte as mentioned above, the concentrated erythrocyte was treated at a falling distance of 1.0 m and filtration was effected until the presence of the concentrated erythrocyte in the blood bag was not confirmed, and the filtered blood was recovered. From the above results, it was found that the average treating rate was 16.6 g/min and the proportion of the residual leukocyte was $10^{-5.99}$ or less.

COMPARATIVE EXAMPLE 11

In Example 10, a nonwoven fabric made of a polyester having an average fiber diameter of 1.2 μm and an average pore diameter of 9.2 μm prepared by a melt-blow method was packed in place of the filter material of this invention and subjected to the same coating treatment as in Example 10 to prepare a filter apparatus. Incidentally, the packing density was adjusted to 0.22 g/cm³. Using this filter apparatus, 325 g of the same concentrated erythrocyte as in Example 10 (RC-MAP, hematocrit: 63%, number of leukocytes: 4,935 cells/μL) was filtered in the same manner as in Example 10 at a falling distance of 1.0 m. As a result, it was found that the average treating rate was 15.8 g/min and the proportion of the residual leukocyte was $10^{-3.98}$.

Though the amounts of the filter materials in the filter apparatus in Example 10 and Comparative Example 11 were the same, it can be seen that in the case of the filter apparatus in Example 10, the leukocyte-removing performance was extremely high as compared with the filter apparatus in Comparative Example 11.

EXAMPLE 11

On the upper stream side of 1.3 g of the same filter material of this invention as in Example 10 were arranged 1.35 g of a nonwoven fabric made of a polyester having an average fiber diameter of 33 μm and a basis weight of 50 g/m², 0.81 g of a nonwoven fabric made of a polyester having an average fiber diameter of 12 μm and a basis weight of 30 g/m² and 0.59 g of a nonwoven fabric made of a polyester having an average fiber diameter of 1.7 μm and a basis weight of 66 g/m², and they were packed in a vessel having an effective sectional area of filtering portion of 45 cm² (6.7 cm×6.7 cm) so that the packing density became 0.22 g/cm³ and then subjected to the same coating treatment as in Example 10 to prepare a filter apparatus.

Using this filter apparatus, 325 g of concentrated erythrocyte (RC-MAP, hematocrit: 62%, number of leukocytes: 6,335 cells/μL) which had been stored at 4° C. for 9 days was filtered in the same manner as in Example 10 at a falling distance of 1.0 m at an average treating rate adjusted to 5.6 g/min. The temperature of the concentrated erythrocyte just before the starting of filtration was 12° C. From the above results, it was found that the proportion of the residual leukocyte was $10^{-4.10}$ and the recovery of erythrocyte was 94.6%.

EXAMPLE 12

Using the same filter apparatus as in Example 11, the same concentrated erythrocyte as in Example 11 (RC-MAP, hematocrit: 62%, number of leukocytes: 6,335 cells/μL) was treated in the same manner as in Example 11 at an average treating rate of 19.8 g/min. As a result, it was found that the proportion of the residual leukocyte was $10^{-3.93}$ and the recovery of erythrocyte was 93.9%.

EXAMPLE 13

On the upper stream side of 1.3 g of the same filter material of this invention as in Example 3 were arranged 1.35 g of a nonwoven fabric made of a polyester having an average fiber diameter of 33 μm and a basis weight of 50 g/m², 0.81 g of a nonwoven fabric made of a polyester having an average fiber diameter of 12 μm and a basis weight of 30 g/m² and 0.59 g of a nonwoven fabric made of a polyester having an average fiber diameter of 1.7 μm and a basis weight of 66 g/m², and they were packed in a vessel having an effective sectional area of filtering portion of 45 cm² (6.7 cm×6.7 cm) so that the packing density became 0.22 g/cm³ and then subjected to the same coating treatment as in Example 10 to prepare a filter apparatus.

Using this filter apparatus, 325 g of concentrated erythrocyte (RC-MAP, hematocrit: 64%, number of leukocytes: 3,387 cells/μL) which had been stored at 4° C. for 10 days was filtered in the same manner as in Example 10 at a falling distance of 1.0 m. The temperature of the concentrated erythrocyte just before the starting of filtration was 12° C. From the above results, it was found that the average treating rate was 24.4 g/min, the proportion of the residual leukocyte was $10^{-3.78}$ and the recovery of erythrocyte was 95.1%.

EXAMPLE 14

The same porous element as used in Example 1 was cut to a size of 25 cm×35 cm, immersed in 375 mL of a culture medium having an acetic acid bacterium concentration of 498 cells/mL and subjected in this state to stationary culture at 28° C. for 14 hours. During the stationary culture, the porous element was turned upside down every two hours. After completion of the stationary culture, washing with a water stream was effected to remove the acetic acid bacterium. According to the above-mentioned production process, there was obtained a filter material in which a reticulate structure composed of cellulose fibers produced by the acetic acid bacterium having an average fiber diameter of 0.02 μm were kept on the surfaces on the front and back sides of the porous element. The acetic acid bacterium used and the composition of the culture medium used were the same as in Example 3. The average fiber diameter of the fiber structure was 0.02 μm, the ratio between the average pore diameter of the porous element and the average fiber diameter of the fiber structure was 460, the ratio between the average fiber diameter of the porous element and the average fiber diameter of the fiber structure was 60, the porosity of the filter material was 85% and the keeping proportion of the fiber structure to the filter material was 0.12% by weight.

On the upper stream side of 1.3 g of this filter material were arranged 1.35 g of a nonwoven fabric made of a polyester having an average fiber diameter of 33 μm and a basis weight of 50 g/cm², 0.81 g of a nonwoven fabric made of a polyester having an average fiber diameter of 12 μm and a basis weight of 30 g/cm² and 0.59 g of a nonwoven fabric made of a polyester having an average fiber diameter of 1.7 μm and a basis weight of 66 g/cm² and they were packed in a vessel having an effective sectional area of filtering portion of 45 cm² (6.7 cm×6.7 cm) so that the packing density became 0.22 g/cm³, and thereafter, subjected to the same coating treatment as in Example 10, to prepare a filter apparatus. Using this filter apparatus, 325 g of the same concentrated erythrocyte as in Example 13 (RC-MAP, hematocrit: 64%, number of leukocytes: 3,387 cells/μL) was filtered in the same manner as in Example 10 at a falling distance of 1.0 m. The temperature of the concentrated erythrocyte just before the starting of filtration was 12° C. From the above results, it was found that the average treating rate was 14.8 g/min, the proportion of the residual leukocyte was $10^{-4.24}$, and the recovery of erythrocyte was 94.2%.

INDUSTRIAL APPLICABILITY

The leukocyte-removing filter material of this invention is useful as a filter material for use in transfusion of blood components because it can remove leukocyte which becomes a cause for side effects with a high efficiency while maintaining a high recovery of useful blood components.

We claim:

1. A leukocyte-removing filter material which is composed of a porous element having an average pore diameter of not less than 1.0 μm but less than 100 μm and a fiber structure having an average fiber diameter of not less than 0.01 μm but less than 1.0 μm kept on the porous element, wherein the porosity of the filter material is not less than 50% but less than 95%, the keeping proportion of the fiber structure to the filter material is not less than 0.01% by weight but less than 30% by weight, and the ratio between the average pore diameter of the porous element and the average fiber diameter of the fiber structure is not less than 2 but less than 2,000 and the fiber structure forms a reticulate structure.

2. The leukocyte-removing filter material according to claim 1, wherein the ratio of the average pore diameter of the porous element to the average fiber diameter of the fiber structure is not less than 10 but less than 1,800.

3. The leukocyte-removing filter material according to claim 1, wherein the keeping proportion of the fiber structure to the filter material is not less than 0.03% by weight but less than 10% by weight.

4. The leukocyte-removing filter material according to claim 1, wherein each of the fibers constructing the fiber structure is a single fiber.

5. The leukocyte-removing filter material according to claim 1, wherein the average fiber diameter of the fiber structure is not less than 0.01 μm but less than 0.8 μm.

6. The leukocyte-removing filter material according to claim 1, wherein the fiber structure is kept on the whole of the porous element.

7. The leukocyte-removing filter material according to claim 6, wherein the fiber structure is substantially uniformly kept substantially on the whole of the porous element.

8. The leukocyte-removing filter material according to claim 1, wherein the fiber structure is kept on the surface of one side of the porous element.

9. The leukocyte-removing filter material according to claim 8, wherein the fiber structure is substantially uniformly kept on the surface.

10. The leukocyte-removing filter material according to claim 1, wherein the fiber structure is kept on the surfaces on both sides of the porous element.

11. The leukocyte-removing filter material according to claim 10, wherein the fiber structure is substantially uniformly kept on the surfaces.

12. The leukocyte-removing filter material according to claim 1, wherein the porous element is a fiber congregation.

13. The leukocyte-removing filter material according to claim 12, wherein the ratio of the average fiber diameter of the fiber congregation to the average fiber diameter of the fiber structure is not less than 10 but less than 1,000.

14. The leukocyte-removing filter material according to claim 13, wherein the fiber congregation is a nonwoven fabric.

15. The leukocyte-removing filter material according to claim 13, wherein the fiber congregation is of long fibers.

16. The leukocyte-removing filter material according to claim 1, wherein the porous element is a spongy interconnected porous material.

17. The leukocyte-removing filter material according to claim 1, wherein the thickness of the filter material in the flow direction is not less than 0.1 mm but less than 30 mm.

18. The leukocyte-removing filter material according to claim 17, wherein the thickness of the filter material in the flow direction is not less than 0.1 mm but less than 15 mm.

19. The leukocyte-removing filter material according to claim 1, wherein the porous element and/or the fiber structure is surface-modified.

20. The leukocyte-removing filter material according to claim 19, wherein the surface of the porous element and/or the fiber structure is coated with a high polymer material.

21. The leukocyte-removing filter material according to claim 20, wherein the surface of the porous element and/or the fiber structure is coated with a high polymer material having a nonionic, hydrophilic group.

22. The leukocyte-removing filter material according to claim 20 or 21, wherein the high polymer material is a copolymer comprising a polymerizable monomer having a basic nitrogen-containing functional group in an amount of 0.1 to 20% as a monomer unit.

23. The leukocyte-removing filter material according to claim 1, wherein the reticulate structure is a uniform reticulate structure.

24. A process for producing a leukocyte-removing filter material which comprises dispersing fibers having an average fiber diameter of not less than 0.01 μm but less than 1.0 μm in a dispersion medium, and keeping the same, by paper-making, on a porous element having an average pore diameter of not less than 1.0 μm but less than 100 μm, wherein the filter material consists of the porous element and a fiber structure composed of a plurality of the fibers; the porosity of the filter material is not less than 50% but less than 95%; the keeping proportion of the fiber structure to the filter material is not less than 0.01% by weight but less than 30% by weight; the ratio between the average pore diameter of the porous element and the average fiber diameter of the fiber structure is not less than 2 but less than 2,000; and the fiber structure forms a reticulate structure.

25. The production process according to claim 24, wherein the fibers having an average fiber diameter of not less than 0.01 μm but less than 1.0 μm are those obtained by cleaving cleavable fibers.

26. The production process according to claim 25, wherein the cleavable fibers are regenerated cellulose fibers.

27. The production process according to claim 26, wherein the method of cleaving the cleavable fibers is a fibrillation method.

28. The production process according to claim 24, which further comprises a step in which the fibers having an average fiber diameter of not less than 0.01 μm but less than 1.0 μm are obtained by culturing a microorganism having an ability to produce cellulose in a liquid culture medium by intermittently or continuously applying a vibration thereto and recovering the fibers from the culture medium.

29. The production process according to claim 28, which further comprises a step of splitting the fibers recovered.

30. The production process according to claim 24, which further comprises a step in which the fibers having an average fiber diameter of not less than 0.01 μm but less than 1.0 μm are obtained by splitting the microorganism-cellulose fiber mass.

31. The process for producing a leukocyte-removing filter material according to claim 24, which comprises dispersing the fibers having an average fiber diameter of not less than 0.01 μm but less than 1.0 μm in a dispersion medium to obtain a fiber dispersion, keeping this dispersion, by paper-making, on a porous element having an average pore diameter of not less than 1.0 μm but less than 100 μm and subsequently subjecting the resulting filter material to a high pressure liquid treatment.

32. A process for producing a leukocyte-removing filter material which comprises allowing a microorganism having an ability to produce cellulose fiber and a porous element having an average pore diameter of not less than 1.0 μm but less than 100 μm in a liquid culture medium, culturing the microorganism in the liquid culture medium, and then recovering the porous element, wherein the filter material consists of the porous element and a fiber structure having an average fiber diameter of not less than 0.01 μm but less than 1.0 μm; the porosity of the filter material is not less than 50% but less than 95%; the keeping proportion of the fiber structure to the filter material is not less than 0.01% by weight but less than 30% by weight; the ratio between the average pore diameter of the porous element and the average fiber diameter of the fiber structure is not less than 2 but less than 2,000; and the fiber structure forms a reticulate structure.

33. The production process according to claim 32, wherein the microorganism having an ability to produce cellulose fiber is an acetic acid bacterium.

34. The production process according to claim 32, wherein the culture is a stationary culture.

35. The production process according to claim 32, wherein the liquid level of the liquid culture medium is intermittently or continuously changed to be allowed to pass through the exterior and interior of the porous element, thereby culturing the microorganism.

36. The production process according to claim 32, wherein the microorganism is cultured while a gas is introduced into the liquid culture medium and/or the interior of the porous element.

37. The production process according to claim 32, which further comprises a step of turning the porous element upside down during the culture.

38. The production process according to claim 32, wherein the microorganism is cultured at a microorganism concentration of not less than one cells/mL but less than $1.0 \times 10^7$ cells/mL.

39. The production process according to claim 32, wherein the culturing time is not less than 0.5 hour but less than 48 hours.

40. A process for producing a leukocyte-removing filter material which comprises spinning a porous element having an average pore diameter of not less than 1.0 μm but less than 100 μm by a melt-blow method and mixing fibers having an average fiber diameter of not less than 0.01 μm but less than 1.0 μm into a fiber bundle stream which is being spun, wherein the filter material consists of the porous element and a fiber structure composed of a plurality of fibers kept on the porous element, the porosity of the filter material is not less than 50% but less than 95%; the keeping proportion of the fiber structure to the filter material is not less than 0.01% by weight but less than 30% by weight; the ratio between the average pore diameter of the porous element and the average fiber diameter of the fiber structure is not less than 2 but less than 2,000; and the fiber structure forms a reticulate structure.

41. The production process according to claim 40 which comprises a step of further subjecting the porous element and the fiber structure kept on the above porous structure to high pressure liquid treatment.

42. An apparatus for removing leukocyte from a leukocyte-containing solution, which comprises 1) a feed opening, 2) a filter material which is composed of a porous element having an average pore diameter of not less than 1.0 μm but less than 100 μm and a fiber structure having an average fiber diameter of not less than 0.01 μm but less than 1.0 μm kept on the porous element and which has a porosity of not less than 50% but less than 95%, and in which filter material the keeping proportion of the fiber structure to the filter material is not less than 0.01% by weight but less than 30% by weight, the ratio between the average pore diameter of the porous element to the average fiber diameter of the fiber structure is not less than 2 but less than 2,000 and the fiber structure forms a reticulate structure; and 3) a discharging opening.

43. The apparatus according to claim 42, wherein a plurality of sheets of the filter material are laminated in the flow direction.

44. The apparatus according to claim 42, wherein on the upper stream side and/or the down stream side of the filter material, other filter materials are arranged.

45. The apparatus according to claim 44, which comprises a filter material for removing fine agglomerates on the upper stream side of the filter material.

46. The apparatus according to claim 42, wherein the sectional area of the filter material in the normal line direction to the flow direction is not less than 3 cm$^2$ but less than 100 cm$^2$.

47. A process for removing leukocyte from a leukocyte-containing solution, which comprises using an apparatus which comprises 1) a feed opening, 2) a filter material which is composed of a porous element having an average pore diameter of not less than 1.0 μm but less than 100 μm and a fiber structure having an average fiber diameter of not less than 0.01 μm but less than 1.0 μm kept on the porous element and which has a porosity of not less than 50% but less than 95% and in which filter material the keeping proportion of the fiber structure to the filter material is not less than 0.01% by weight but less than 30% by weight, the ratio between the average pore diameter of the porous element to the average fiber diameter of the fiber structure is not less than 2 but less than 2,000 and the fiber structure forms a reticulate structure; and 3) a discharging opening; pouring the leukocyte-containing solution to the feed opening; and recovering a liquid filtered by the filter material from the discharging opening.

48. The process according to claim 47, wherein the leukocyte-containing solution is a whole blood preparation, a concentrated erythrocyte preparation or a platelet concentrate preparation.

49. The process according to claim 48, wherein the leukocyte-containing solution is a whole blood preparation or a concentrated erythrocyte preparation and the apparatus volume is not less than 3 mL but less than 20 mL per one unit.

50. The process according to claim 49, wherein the leukocyte-containing solution is a whole blood preparation or a concentrated erythrocyte preparation and the number of the remaining leukocytes in the recovered solution is less than $1 \times 10^3$ cells/unit.

51. The process according to claim 48, wherein the leukocyte-containing solution is a platelet concentrate preparation and the apparatus volume per 5 units is not less than 1 mL but less than 10 mL.

52. The process according to claim 51, wherein the leukocyte-containing solution is a platelet concentrate preparation and the number of the remaining leukocytes in the recovered solution is less than $1 \times 10^3$ cells/5 units.

53. The process according to claim 47, wherein the leukocyte-containing solution is a body fluid, the leukocyte-containing solution is continuously introduced to the feed opening and a liquid filtered by the filter is recovered from the discharge opening.

* * * * *